(12) United States Patent
Tehrani

(10) Patent No.: US 8,255,056 B2
(45) Date of Patent: Aug. 28, 2012

(54) BREATHING DISORDER AND PRECURSOR PREDICTOR AND THERAPY DELIVERY DEVICE AND METHOD

(75) Inventor: Amir J. Tehrani, Redwood City, CA (US)

(73) Assignee: RMX, LLC, San Francisco, CA (US)

( * ) Notice: Subject to any disclaimer, the term of this patent is extended or adjusted under 35 U.S.C. 154(b) by 858 days.

(21) Appl. No.: 10/966,421

(22) Filed: Oct. 15, 2004

(65) Prior Publication Data

US 2005/0085866 A1     Apr. 21, 2005

Related U.S. Application Data

(63) Continuation-in-part of application No. 10/686,891, filed on Oct. 15, 2003.

(51) Int. Cl.
*A61N 1/18* (2006.01)
(52) U.S. Cl. .......................................... 607/42
(58) Field of Classification Search ............... 607/42
See application file for complete search history.

(56) References Cited

U.S. PATENT DOCUMENTS

| | | | |
|---|---|---|---|
| 3,773,051 A | 11/1973 | Holcomb et al. | |
| 4,827,935 A | 5/1989 | Geddes | |
| 4,830,008 A | 5/1989 | Meer | 128/421 |
| 5,056,519 A | 10/1991 | Vince | 128/419 |
| 5,146,918 A | 9/1992 | Kallok et al. | 128/419 |
| 5,174,287 A | 12/1992 | Kallok et al. | 128/419 |
| 5,190,036 A | 3/1993 | Linder | |
| 5,211,173 A | 5/1993 | Kallok et al. | 128/419 |
| 5,215,082 A | 6/1993 | Kallok et al. | 128/419 |
| 5,233,983 A | 8/1993 | Markowitz | 607/42 |
| 5,265,604 A | 11/1993 | Vince | 607/42 |
| 5,281,219 A | 1/1994 | Kallok | 607/42 |
| 5,300,094 A | 4/1994 | Kallok et al. | 607/42 |
| 5,423,327 A | 6/1995 | Clauson et al. | 128/716 |
| 5,483,969 A | 1/1996 | Testerman et al. | |
| 5,485,851 A | 1/1996 | Erickson | 128/716 |
| 5,522,862 A | 6/1996 | Testerman et al. | 607/42 |
| 5,524,632 A | 6/1996 | Stein et al. | 128/733 |
| 5,540,731 A | 7/1996 | Testerman | 607/42 |
| 5,540,732 A | 7/1996 | Testerman et al. | 607/42 |

(Continued)

FOREIGN PATENT DOCUMENTS

DE     112004001957 T5     8/2006

(Continued)

OTHER PUBLICATIONS

Don D. Sin, Effects of Continuous Positive Airway Pressure on Cardiovascular Outcomes in Heart Failure Patients With and Without Cheyne-Stokes Respiration, *Circulation*, 102:61-66 (Jul. 4, 2000).

(Continued)

*Primary Examiner* — George Manuel
*Assistant Examiner* — Alyssa M Alter
(74) *Attorney, Agent, or Firm* — Levine Bagade Han LLP

(57) ABSTRACT

A device and method for sensing breathing disorders, irregularities or insufficiencies is provided. One aspect includes sensing a precursor to an onset of a breathing disorder or episode of a breathing disorder and responding to sensing the precursor. Another aspect includes responding to treat the breathing disorder before manifestation of the disorder. Another aspect includes identifying a likelihood of a breathing disorder and responding using the likelihood and other information indicating onset or occurrence of a breathing disorder.

51 Claims, 12 Drawing Sheets

U.S. PATENT DOCUMENTS

| | | | | |
|---|---|---|---|---|
| 5,540,733 | A | 7/1996 | Testerman et al. | 607/42 |
| 5,549,655 | A | 8/1996 | Erickson | |
| 5,572,543 | A | 11/1996 | Heinemann et al. | |
| 5,678,535 | A | 10/1997 | DiMarco | 128/200.24 |
| 5,766,228 | A | 6/1998 | Bonnet et al. | 607/16 |
| 5,797,923 | A | 8/1998 | Aiyar et al. | 606/129 |
| 5,800,470 | A | 9/1998 | Stein et al. | 607/20 |
| 5,814,086 | A | 9/1998 | Hirschberg et al. | |
| 5,830,008 | A | 11/1998 | Broschard, III | |
| 5,876,353 | A | 3/1999 | Riff | 607/547 |
| 5,895,360 | A | 4/1999 | Christopherson et al. | 600/529 |
| 5,911,218 | A * | 6/1999 | DiMarco | 128/200.24 |
| 5,944,680 | A | 8/1999 | Christopherson | |
| 6,021,352 | A | 2/2000 | Christopherson et al. | 607/42 |
| 6,099,479 | A | 8/2000 | Christopherson et al. | 600/529 |
| 6,212,435 | B1 | 4/2001 | Lattner et al. | 607/134 |
| 6,224,562 | B1 | 5/2001 | Lurie et al. | 601/41 |
| 6,251,126 | B1 | 6/2001 | Ottenhoff et al. | 607/42 |
| 6,269,269 | B1 | 7/2001 | Ottenhoff et al. | 607/42 |
| 6,312,399 | B1 | 11/2001 | Lurie et al. | |
| 6,314,324 | B1 | 11/2001 | Lattner et al. | |
| 6,345,202 | B2 | 2/2002 | Richmond et al. | 607/42 |
| 6,415,183 | B1 * | 7/2002 | Scheiner et al. | 607/42 |
| 6,463,327 | B1 | 10/2002 | Lurie et al. | |
| 6,480,733 | B1 | 11/2002 | Turcott | 600/516 |
| 6,489,447 | B1 | 12/2002 | Basey et al. | |
| 6,512,949 | B1 | 1/2003 | Combs et al. | |
| 6,527,729 | B1 | 3/2003 | Turcott | 600/528 |
| 6,542,774 | B2 | 4/2003 | Hill | |
| 6,572,543 | B1 | 6/2003 | Christopherson et al. | 600/300 |
| 6,574,507 | B1 | 6/2003 | Bonnet | 607/20 |
| 6,587,725 | B1 | 7/2003 | Durand et al. | |
| 6,587,726 | B2 | 7/2003 | Lurie et al. | |
| 6,589,188 | B1 | 7/2003 | Street et al. | 600/538 |
| 6,600,949 | B1 | 7/2003 | Turcott | 600/518 |
| 6,633,779 | B1 | 10/2003 | Schuler et al. | |
| 6,651,652 | B1 | 11/2003 | Ward | 128/200.24 |
| 6,731,984 | B2 | 5/2004 | Cho et al. | 607/17 |
| 6,735,479 | B2 | 5/2004 | Fabian et al. | |
| 6,752,765 | B1 | 6/2004 | Jensen et al. | 600/536 |
| 6,770,022 | B2 | 8/2004 | Mechlenburg et al. | |
| 6,811,537 | B2 | 11/2004 | Bardy | |
| 6,830,548 | B2 | 12/2004 | Bonnet et al. | 600/529 |
| 6,881,192 | B1 | 4/2005 | Park et al. | |
| 6,908,437 | B2 | 6/2005 | Bardy | |
| 7,058,453 | B2 | 6/2006 | Nelson et al. | |
| 7,070,568 | B1 | 7/2006 | Koh et al. | |
| 7,082,331 | B1 | 7/2006 | Park et al. | |
| 7,117,032 | B2 | 10/2006 | Childre et al. | |
| 7,277,757 | B2 | 10/2007 | Casavant et al. | |
| 7,532,934 | B2 | 5/2009 | Lee et al. | |
| 7,610,094 | B2 | 10/2009 | Stahmann et al. | |
| 7,840,270 | B2 | 11/2010 | Ignagni et al. | |
| 7,970,475 | B2 | 6/2011 | Tehrani et al. | |
| 7,979,128 | B2 | 7/2011 | Tehrani et al. | |
| 8,116,872 | B2 | 2/2012 | Tehrani et al. | |
| 2002/0049482 | A1 | 4/2002 | Fabian et al. | |
| 2002/0193697 | A1 | 12/2002 | Cho et al. | 600/529 |
| 2002/0193839 | A1 | 12/2002 | Cho et al. | 607/17 |
| 2003/0127091 | A1 | 7/2003 | Chang | |
| 2003/0153953 | A1 | 8/2003 | Park et al. | 607/17 |
| 2003/0153954 | A1 | 8/2003 | Park et al. | 607/17 |
| 2003/0153955 | A1 | 8/2003 | Park et al. | 607/17 |
| 2003/0153956 | A1 | 8/2003 | Park et al. | 607/17 |
| 2003/0195571 | A1 | 10/2003 | Burnes et al. | 607/9 |
| 2003/0204213 | A1 | 10/2003 | Jensen et al. | |
| 2003/0225339 | A1 | 12/2003 | Orr et al. | |
| 2004/0044377 | A1 | 3/2004 | Larsson | |
| 2004/0059240 | A1 | 3/2004 | Cho et al. | |
| 2004/0077953 | A1 | 4/2004 | Turcott | |
| 2004/0088015 | A1 | 5/2004 | Casavant et al. | 607/14 |
| 2004/0111040 | A1 | 6/2004 | Ni et al. | 600/534 |
| 2004/0116784 | A1 | 6/2004 | Gavish | |
| 2004/0122484 | A1 | 6/2004 | Hatlestad et al. | |
| 2004/0134496 | A1 | 7/2004 | Cho et al. | 128/204.23 |
| 2004/0138719 | A1 | 7/2004 | Cho et al. | 607/42 |
| 2004/0176809 | A1 | 9/2004 | Cho et al. | 607/14 |
| 2004/0199221 | A1 | 10/2004 | Fabian et al. | |
| 2004/0225226 | A1 | 11/2004 | Lehrman et al. | 600/529 |
| 2004/0237963 | A1 | 12/2004 | Berthon-Jones | 128/204.26 |
| 2005/0021102 | A1 | 1/2005 | Ignagni et al. | |
| 2005/0039745 | A1 | 2/2005 | Stahmann et al. | |
| 2005/0043644 | A1 | 2/2005 | Stahmann et al. | 600/529 |
| 2005/0043772 | A1 * | 2/2005 | Stahmann et al. | 607/42 |
| 2005/0055060 | A1 | 3/2005 | Koh et al. | 607/17 |
| 2005/0061315 | A1 | 3/2005 | Lee et al. | 128/204.21 |
| 2005/0061319 | A1 | 3/2005 | Hartley et al. | 128/204.18 |
| 2005/0061320 | A1 | 3/2005 | Lee et al. | 128/204.18 |
| 2005/0065563 | A1 | 3/2005 | Scheiner | 607/9 |
| 2005/0065567 | A1 | 3/2005 | Lee et al. | 607/17 |
| 2005/0074741 | A1 | 4/2005 | Lee et al. | 434/433 |
| 2005/0076909 | A1 | 4/2005 | Stahmann et al. | |
| 2005/0080461 | A1 | 4/2005 | Stahmann et al. | 607/17 |
| 2005/0085734 | A1 | 4/2005 | Tehrani | |
| 2005/0085865 | A1 | 4/2005 | Tehrani | |
| 2005/0085867 | A1 | 4/2005 | Tehrani | |
| 2005/0085868 | A1 | 4/2005 | Tehrani et al. | |
| 2005/0085869 | A1 | 4/2005 | Tehrani | |
| 2005/0101833 | A1 | 5/2005 | Hsu et al. | 600/26 |
| 2005/0107860 | A1 | 5/2005 | Ignagni et al. | 607/116 |
| 2005/0115561 | A1 | 6/2005 | Stahmann et al. | 128/200.24 |
| 2005/0119711 | A1 | 6/2005 | Cho et al. | |
| 2005/0145246 | A1 | 7/2005 | Hartley et al. | 128/203.14 |
| 2005/0148897 | A1 | 7/2005 | Cho et al. | 600/533 |
| 2005/0165457 | A1 | 7/2005 | Benser et al. | |
| 2005/0224076 | A1 | 10/2005 | Pflchner et al. | |
| 2005/0240240 | A1 | 10/2005 | Park et al. | 607/42 |
| 2005/0261600 | A1 | 11/2005 | Aylsworth | |
| 2005/0261747 | A1 | 11/2005 | Schuler et al. | |
| 2006/0030894 | A1 | 2/2006 | Tehrani | |
| 2006/0036294 | A1 | 2/2006 | Tehrani | |
| 2006/0058852 | A1 | 3/2006 | Koh et al. | |
| 2006/0064030 | A1 | 3/2006 | Cosentino et al. | |
| 2006/0064325 | A1 | 3/2006 | Matsumoto et al. | |
| 2006/0122661 | A1 | 6/2006 | Mandell | |
| 2006/0122662 | A1 | 6/2006 | Tehrani | |
| 2006/0142815 | A1 | 6/2006 | Tehrani et al. | |
| 2006/0149334 | A1 | 7/2006 | Tehrani et al. | |
| 2006/0155341 | A1 | 7/2006 | Tehrani et al. | |
| 2006/0167523 | A1 | 7/2006 | Tehrani et al. | |
| 2006/0224211 | A1 | 10/2006 | Durand et al. | |
| 2006/0247729 | A1 | 11/2006 | Tehrani et al. | |
| 2006/0282131 | A1 | 12/2006 | Caparso et al. | |
| 2007/0021795 | A1 | 1/2007 | Tehrani | |
| 2007/0156199 | A1 | 7/2007 | Koh et al. | |
| 2008/0021506 | A1 | 1/2008 | Grocela | |
| 2008/0167695 | A1 | 7/2008 | Tehrani et al. | |
| 2008/0177347 | A1 | 7/2008 | Tehrani et al. | |
| 2008/0183239 | A1 | 7/2008 | Tehrani et al. | |
| 2008/0183240 | A1 | 7/2008 | Tehrani et al. | |
| 2008/0188903 | A1 | 8/2008 | Tehrani et al. | |
| 2008/0188904 | A1 | 8/2008 | Tehrani et al. | |
| 2008/0208281 | A1 | 8/2008 | Tehrani et al. | |
| 2011/0230932 | A1 | 9/2011 | Tehrani et al. | |

FOREIGN PATENT DOCUMENTS

| | | | |
|---|---|---|---|
| DE | 112004001953 | T5 | 10/2006 |
| DE | 112004001954 | T5 | 10/2006 |
| WO | WO/8600234 | | 1/1986 |
| WO | WO 2005/037077 | | 4/2005 |
| WO | WO 2005/037172 | | 4/2005 |
| WO | WO 2005/037173 | | 4/2005 |
| WO | WO 2005/037174 | | 4/2005 |
| WO | WO 2005/037220 | | 4/2005 |
| WO | WO 2005/037366 | | 4/2005 |
| WO | WO 2007/058938 | | 5/2007 |

OTHER PUBLICATIONS

Takaomi Taira, M.D., Ph.D., et. al, Phrenic Nerve Stimulation for Diaphragm Pacing With a Spinal Cord Stimulator *Surg Neurol*, 59:128-132 (2003).

Donald B. Shaul, et. al, Thoracoscopic Placement of Phrenic Nerve Electrodes for Diaphragmatic Pacing in Children *Journal of Pediatric Surgery*, 37:974-978 (Jul. 2002).

Christopher Reeve, New Implantable Breathing Device, *University Hospitals of Cleveland*, pp. 1-4, (2003).

Christopher Reeve, Christopher Reeve Paralysis Foundation Questions & Answers, pp. 1-3 (Mar. 13, 2003).

T. Mitsuyana, et. al, Diaphragm Pacing With the Spinal Cord Stimulator, *Aeta Neurochir*, 87:89-92 (2003).

Harish Aiyar, et. al, Laparoscopic Implant Device for Intermuscular Electrodes, IEEE-EMBC and CMBCC, pp. 1167-1168, ((1995).

Harish Aiyar,et.al, Laparoscopic Implant Instrument for the Placement of Intramuscular Electrodes in the Diaphragm, *Transactions on Rehabilitation Engineering*, pp. 360-371 (Sep. 1999).

Anthony F. DiMarco, et. al, Phrenic Nerve Pacing in a Tetraplegic Patient via Intramuscula Diaphragm Electrodes*American Journal of Respiratory and Critical Care Medicine*, 144:1604-1606 (2002).

S.Sauermann, et. al, Computer Aided Adjustment of the Phrenic Pacemaker: Automatic Functions, Documentation, and Quality Control, *Artificial Organs*, 21(3):216-218 (1997).

B.D. Schmit, et. al, An Implantable Impedance Pneumograph Monitor for Detection of Diaphragm Contraction and Airway Obstruction During Diaphragm Pacing, *Medical & Biological Engineering & Computing*, 37:162-168 (1999).

Brian D. Schmit, et. al, Laparoscopic Placement of Electrodes for Diaphragm Pacing Using Stimulation to Locate the Phrenic Nerve Motor Points, *Transactions on Rehabilitation Engineering*, 6(4):382-390 (Dec. 1998).

W. Glenn "Diaphragm Pacing: Present Status" PACE vol. 1 p. 357-370 (1978).

Harish, A. et al, "Laparoscopic Implant Device for Intermuscular Electrodes," *IEEE-EMBC and CMBCC*, pp. 1167-1168, 1995.

Shier, D. et al, *Hole's Human Anatomy & Physiology*,pp. 798 (2 pages total).

U.S. Appl. No. 11/271,554, filed Nov. 10, 2005 in the name of Tehrani et al., final Office Action mailed Jan. 31, 2011.

U.S. Appl. No. 11/981,800, filed Oct. 31, 2007 in the name of Tehrani et al., final Office Action mailed Jan. 20, 2011.

U.S. Appl. No. 11/480,074, filed Jun. 29, 2006 in the name of Tehrani et al., non-final Office Action mailed Mar. 16, 2011.

U.S. Appl. No. 10/686,891, filed Oct. 15, 2003 in the name of Tehrani , non-final Office Action mailed Mar. 30, 2011.

U.S. Appl. No. 10/966,474, filed Oct. 15, 2004 in the name of Tehrani et al., non-final Office Action mailed Mar. 30, 2011.

U.S. Appl. No. 11/981,727, filed Oct. 31, 2007 in the name of Tehrani et al., non-final Office Action mailed Apr. 4, 2011.

U.S. Appl. No. 11/249,718, filed Oct. 13, 2005 in the name of Tehrani, non-final Office Action mailed Apr. 1, 2011.

U.S. Appl. No. 11/271,726, filed Nov. 10, 2005 in the name of Tehrani et al., non-final Office Action mailed Apr. 4, 2011.

U.S. Appl. No. 11/271,264, filed Nov. 10, 2005 in the name of Tehrani et al., final Office Action mailed Apr. 7, 2011.

Heinzer, R., et al, "Lung Volume and Continuous Positive Airway Pressure Requirements in Obstructive Sleep Apeau" *American Journal of Respiratory and Critical Care Medicine*, vol. 172, pp. 114-117, 2005.

DiMarco, A F., "Combined Intercostal and Diaphragm Pacing to Provide Artificial Ventilation in Patients With Tetraplegia" *Arch Phys Med Rehabil*, vol. (86), pp. 1200-1207, 2005.

Dunn, R., "Diaphragm and Accessory Respiratory Muscle Stimulation Using Intramuscular Electrodes" *Arch Phys Med Rehabil*, vol. (76), pp. 266-271, 1995.

Glenn, W., et al. "Diaphragm Pacing" *Journal of Thoracic and Cardiovascular Surgery*, vol. (75):2, pp. 273-281, 1978.

"Quadripolar Pacing Addresses Issues Without Moving Leads," *Diagnostic & Invasive Cardiology*, 1 page, Jun. 1, 2010, Scranton Gillette Communications.

Abraham, W., "Advances in Heart Failure Therapy in the Primary Care Context," *Medscape Family Medicine/Primary Care*, 7 pages, 2004.

Arzt, M. et al, "Treatment of Sleep Apnea in Heart Failure," *AJRCCM*, 36 pages, Mar. 9, 2006.

Boston Scientific, "Diaphragm Stimulation During Daily LV Lead Impedance Measurements", Product Education Brochure, 2 pages, Sep. 26, 2008.

Bradley, T.D. et al, "Sleep Apnea and Heart Failure, Part I: Obstructive Sleep Apnea," *Circulation*, pp. 1671-1678, Apr. 1, 2003.

Fessler, H.E., "Heart-Lung Interactions: Applications in the Critically Ill," *Eur. Respir. J.*, vol. 10, pp. 226-237, 1997.

Fichter, J. et al, "Sleep-Related Breathing Disorders are Associate with Ventricular Arrhythmias in Patients with an Implantable Cardioverter-Defibrillator," *Chest*,vol. 122, pp. 558-561, Aug. 2002.

Garrigue, S. et al "Sleep Apnea: A New Indicaton for Cardiac Pacing?," *Pace*, vol. 27, pp. 204-211, Feb. 2004.

Hayano, J. et al "Respiratory Sinus Arrhythmia: A Phenomenon Improving Pulmonary Gas Exchange and Circulatory Efficiency," *Circulation*, vol. 94, pp. 842-847, 1996.

Hennersdorf, M.G. et al, "Chemoreflexsensitivity in Chronic Heart Failure Patients," *European Journal of Heart Failure*, vol. 3, pp. 679-684, 2001.

Ishii, K. et al "Effects of Bilateral Transvenous Diaphragm Pacing on Hemodynamic Function in Patients after Cardiac Operations," *J Thorac Cardrovasc Surg*, vol. 100, pp. 108-114, 1990.

Javaheri, S. et al, "Sleep Apnea in 81 Ambulatory Male Patients with Stable Heart Failure: Types and Their Prevalences, Consequences, and Presentations," *Circulation*, vol. 97, pp. 2154-2159, 1998.

Kohnlein, T. et al, "Central Sleep Apnea Syndrome in Patients with Chronic Heart Disease: a Critical Review of the Current Literature," *Thorax*, vol. 57, pp. 547-554, 2002.

Krachman, S. et al "Comparison of Oxygen Therapy with Nasal Continuous Positive Airway Pressure on Cheyne-Stokes Respiration During Sleep in Congestive Heart Failure," *Chest*, vol. 116, pp. 1550-1557, Dec. 1999.

LaFond, C. et al "Impact of CPAP on Asthmatic Patients with Obstructive Sleep Apnoea," *Eur Respir J*, vol. 29, pp. 307-311, 2007.

Lanfranchi, P.A. et al, "Prognostic Value of Nocturnal Cheyne-Stokes Respiration in Chronic Heart Failure," *Circulation*, pp. 1435-1440, 1999.

Leung, R. et al, "Sleep Apnea and Cardiovascular Disease," *Am J Respir Crit Care Med*, vol. 164, pp. 2147-2165, 2001.

Mathew, O., "Effects of Transient Intrathoracic Pressure Changes (hiccups) on Systemic Arterial Pressure," *J Appl Physiol*, vol. 83, pp. 371-375, 1997.

Norton, J., "Toward Consistent Definitions for Preload and Afterload," *Advan in Physiol Edu*, vol. 25, pp. 53-61, Mar. 2001.

Peters, J. et al, "Negative Intrathoracic Pressue Decreases Independently Left Ventricular Filling and Emptying," *American Physiological Society*, pp. H120-H131, 1989.

Pinsky, M. "Cardiovascular Issues in Respiratory Care," *Chest*, vol. 128, pp. 592-597, Nov. 2005.

Schultz, R. et al "Nocturnal Periodic Breathing in Primary Pulmonary Hypertension," *Eur Respir J*, vol. 19, pp. 658-663, 2002.

Series, F. et al, "Assessment of Upper Airway Stabilizing Forces with the Use of Phrenic Nerve Stimulation in Conscious Humans," *J Appl Physiol*, vol. 94, pp. 2289-2295, 2003.

Sorli, J. et al., "Ventilatory Assist Using Electrical Stimulation of AJdominal Muscles," *IEEE Transactions on Rehabilitation Engineering*, vol. 4, No. 1, pp. 1-6, Mar. 1996.

Van Houwelingen, K. et al "The Sleep Apnoea Syndromes," *European Heart Journal*, vol. 20, pp. 858-866, Jun. 1999.

Viasys Healthcare, "Ventilation Requires Perfect Balance", SensorMedics® 3100A HFOV, VIASYS Healthcare Brochure, 2 pages.

Wolk, R. et al "Sleep-Disordered Breathing and Cardiovascular Disease," *Circulation*, vol. 108, pp. 9-12, Jul. 2003.

Yim, S. et al "Continuous Positive Airway Pressure for Asthma: Not a Big Stretch?," *Eur Respir J*, vol. 29, pp. 226-228, 2007.

Bernardi, L. et al, "Effect of Rosary Prayer and Yoga Mantras on Autonomic Cardiovascular Rhythms: Comparative Study," *BMJ*, 323:22-29, Dec. 2001.

Bernardi, L. et al, "Slow Breathing Increases Arterial Baroreflex sensitivity in Patients with Chronic Heart Failure," *Circulation*,2002.

Gosselink, R. "Controlled Breathing and Dyspnea in Patients With Chronic Obstructive Pulmonary Disease," *Journal of Rehabilitaiton Research and Development*, 40(5):20-34, Supplement 2, Sep./Oct. 2003.

Iazzo, P. ed., "Handbook of Cardiac Anatomy, Physiology, and Devices", p. 398, 2009.

Jensen, A. et al, "Signal Transduction in Smooth Muscle: Airway caliber in healthy and asthmatic subjects effects of bronchial challenge and deep inspirations," *J. Appl Physiol*, 91:506-515, 2001.

Liem, L.B., "EP 101: Ventricular Tachycardia", *EP Lab Digest*, v.7, No. 8, Aug. 2007.

Malkin R. et al., "The Effect of Inducing Ventricular Fibrillation with 50-Hz Pacing Versus T are Stimulation on the Ability to Defibrillate", *Pacing and Clinical Electrophysiology*, vol. 21, issue 5, May 1998.

Patroniti, M.D., et al "Sigh Improves Gas Exchange and Lung Volume in Patients with Acute Respiratory Distress Syndrome Undergoing Pressure Support Ventilation," *Anesthesiology*,96:788-794, 2002.

Series, F. et al, "Increasing the Functional Residual Capacity May Reverse Obstructive Sleep Apnea Sleep," 11(4):349-353, 1988.

Simon, P. et al, "Vagal Feedback in the Entrainment of Respiration to Mechanical Ventilation in Sleeping Humans," *J. App. Physiol*, 89:760-769, 2000.

U.S. Appl. No. 10/686,891, filed Oct. 15, 2003 in the name of Tehrani, non-final Office Action mailed Sep. 18, 2009.

U.S. Appl. No. 11/246,439, filed Oct. 11, 2005 in the name of Tehrani, non-final Office Action mailed Sep. 30, 2009.

U.S. Appl. No. 11/249,718, filed Oct. 13, 2005 in the name of Tehrani, non-final Office Action mailed Apr. 18, 2008.

U.S. Appl. No. 11/249,718, filed Oct. 13, 2005 in the name of Tehrani, Final Office Action mailed Apr. 1, 2009.

U.S. Appl. No. 11/249,718, filed Oct. 13, 2005 in the name of Tehrani, non-final Office Action mailed Nov. 25, 2009.

U.S. Appl. No. 11/981,800, filed Oct. 31, 2007 in the name of Tehrani et al., non-final Office Action mailed Oct. 7, 2009.

U.S. Appl. No. 11/271,554, filed Nov. 10, 2005 in the name of Tehrani et al., non-final Office Action mailed Dec. 24, 2009.

U.S. Appl. No. 11/981,831, filed Oct. 31, 2007 in the name of Tehrani et al., non-final Office Action mailed Jan. 6, 2010.

U.S. Appl. No. 10/966,474, filed Oct. 15, 2004 in the name of Tehrani, Final Office Action mailed Jan. 21, 2010.

U.S. Appl. No. 10/966,472, filed Oct. 15, 2004 in the name of Tehrani et al., non-final Office Action mailed Feb. 23, 2010.

U.S. Appl. No. 11/526,949, filed Sep. 25, 2006 in the name of Tehrani, Final Office Action mailed Mar. 19, 2010.

U.S. Appl. No. 11/271,726, filed Nov. 10, 2005 in the name of Tehrani et al., non-final Office Action mailed Mar. 31, 2010.

U.S. Appl. No. 11/271,264, filed Nov. 10, 2005 in the name of Tehrani et al., non-final Office Action mailed Mar. 30, 2010.

U.S. Appl. No. 11/271,315, filed Nov. 10, 2005 in the name of Tehrani et al., Final Office Action mailed Mar. 31, 2010.

U.S. Appl. No. 11/271,315, filed Nov. 10, 2005 in the name of Tehrani et al., non-final Office Action mailed Oct. 3, 2008.

U.S. Appl. No. 11/981,342, filed Oct. 31, 2007 in the name of Tehrani et al., non-final Office Action mailed Apr. 15, 2010.

U.S. Appl. No. 11/480,074, filed Jun. 29, 2006 in the name of Tehrani et al., Final Office Action mailed Apr. 30, 2010.

U.S. Appl. No. 12/080,133, filed Apr. 1, 2008 in the name of Tehrani et al., non-final Office Action mailed Jun. 10, 2010.

U.S. Appl. No. 11/246,439, filed Oct. 11, 2005 in the name of Tehrani, final Office Action mailed Jun. 29, 2010.

U.S. Appl. No. 11/249,718, filed Oct. 13, 2005 in the name of Tehrani, final Office Action mailed Sep. 14, 2010.

U.S. Appl. No. 10/686,891, filed Oct. 15, 2003 in the name of Tehrani, final Office Action mailed Sep. 15, 2010.

U.S. Appl. No. 11/526,949, filed Sep. 25, 2006 in the name of Tehrani, non-final Office Action mailed Oct. 5, 2010.

U.S. Appl. No. 11/981,342, filed Oct. 31, 2007 in the name of Tehrani et al., final Office Action mailed Oct. 7, 2010.

\* cited by examiner

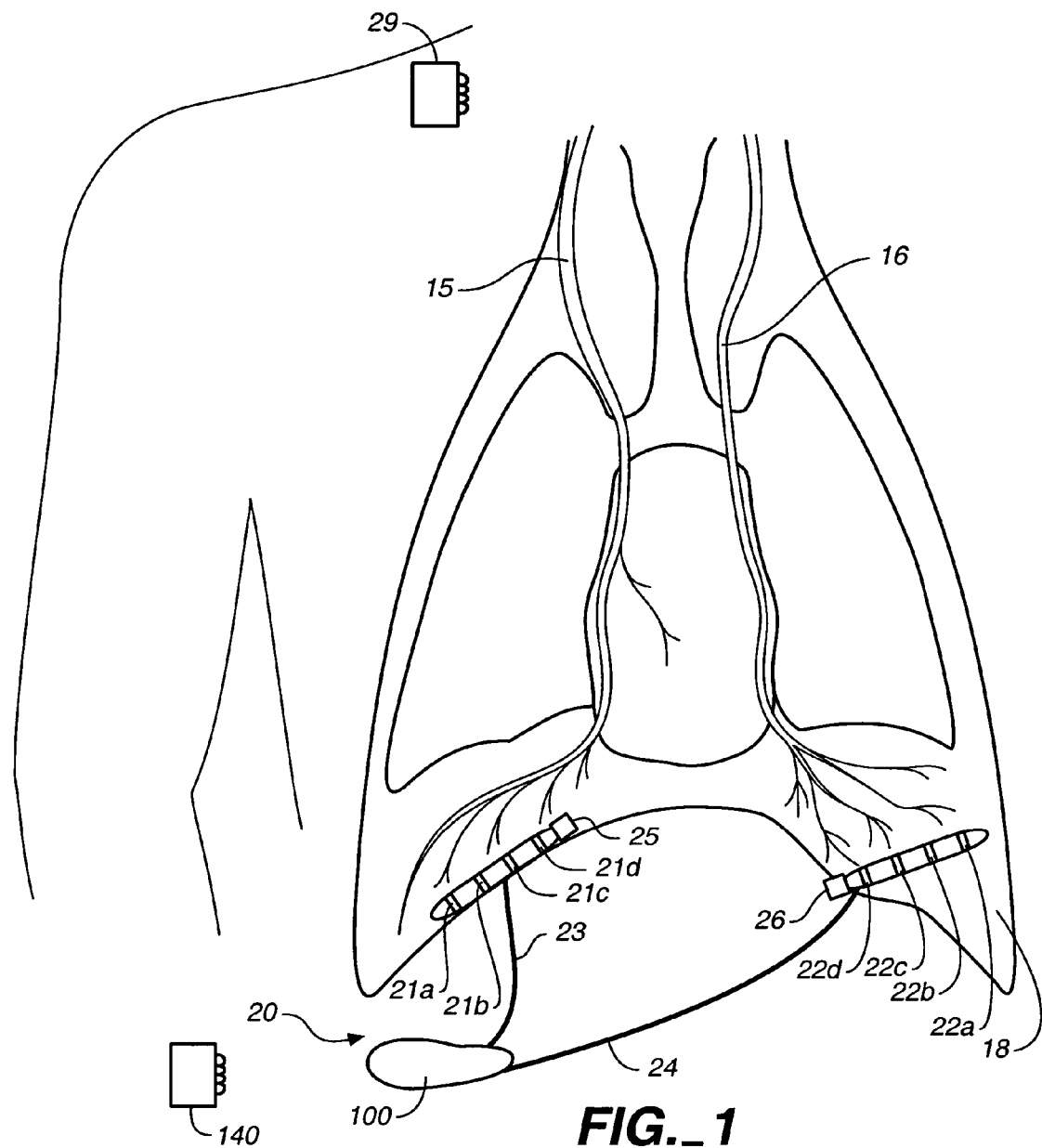
FIG._1

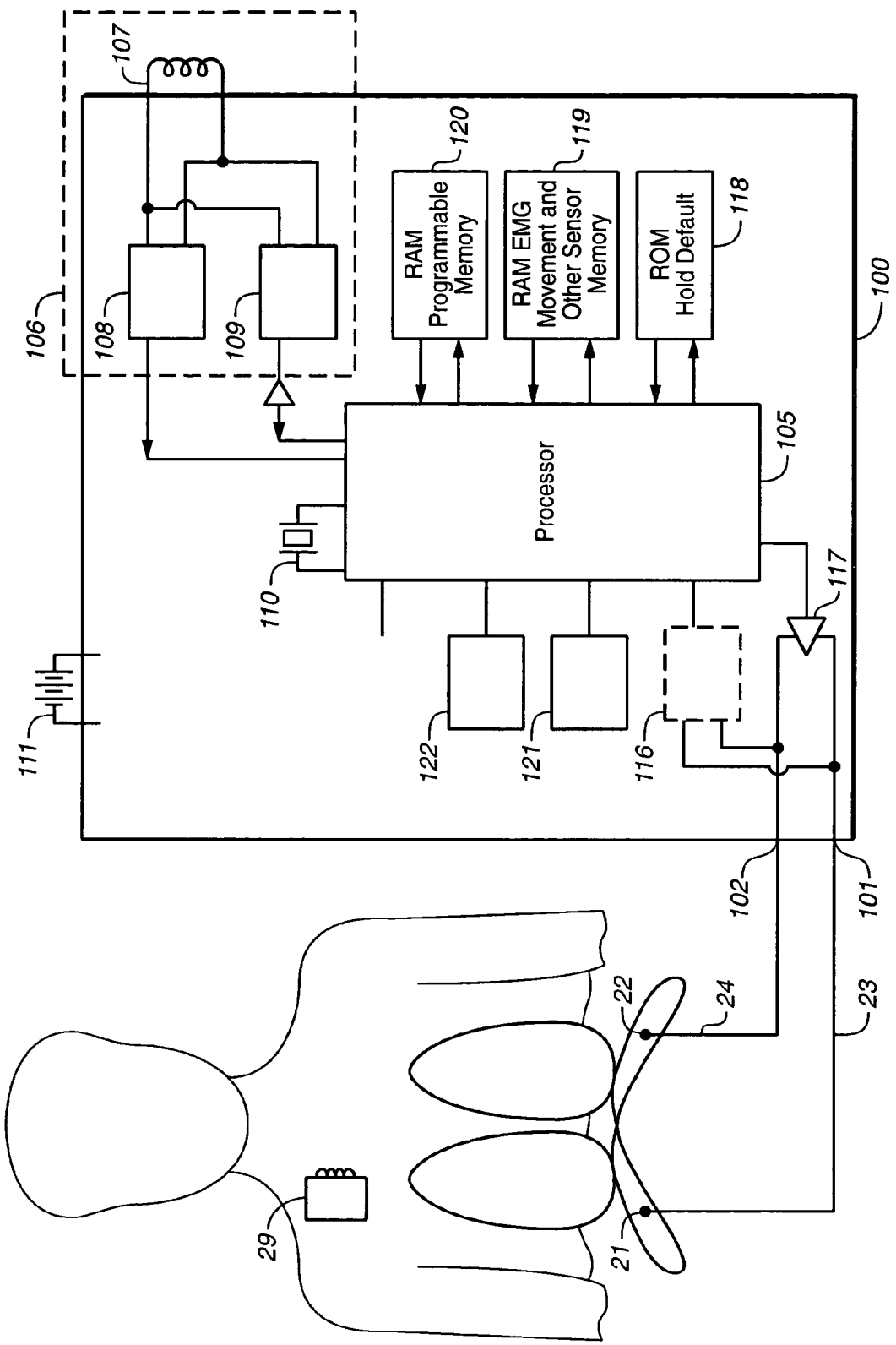
FIG._2

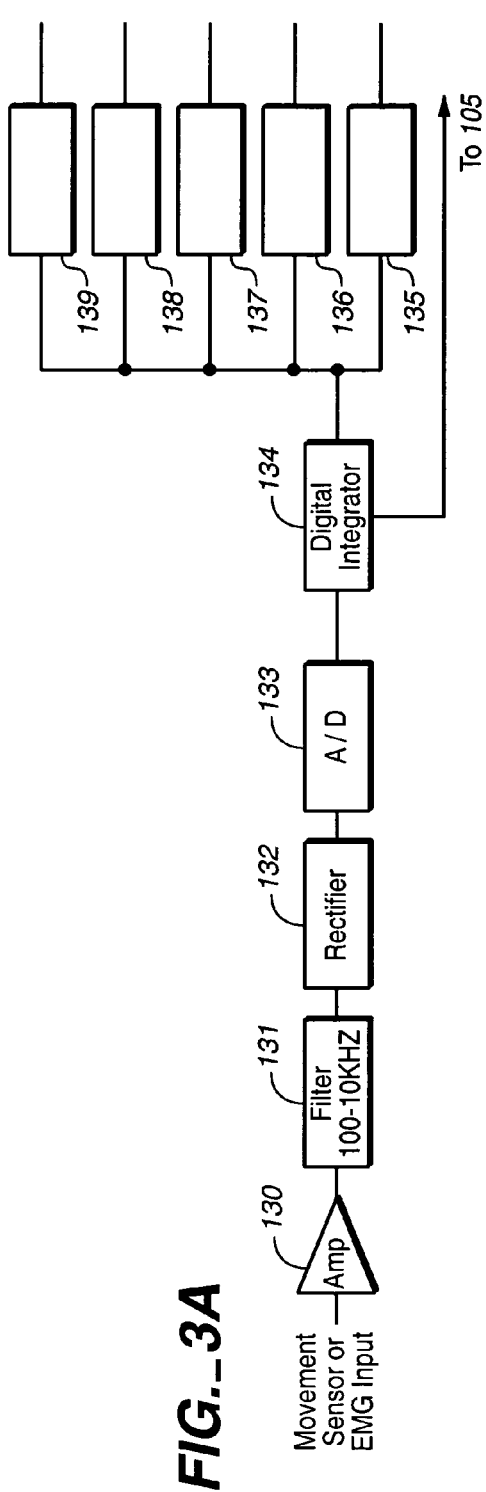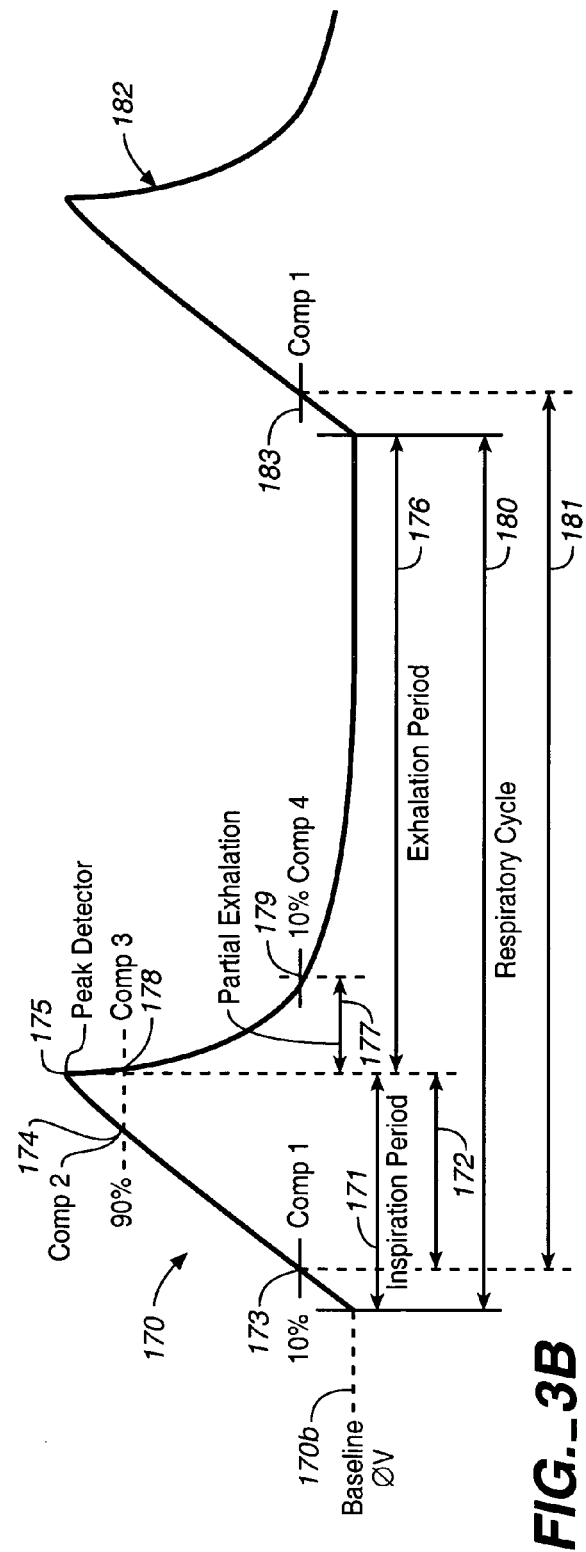

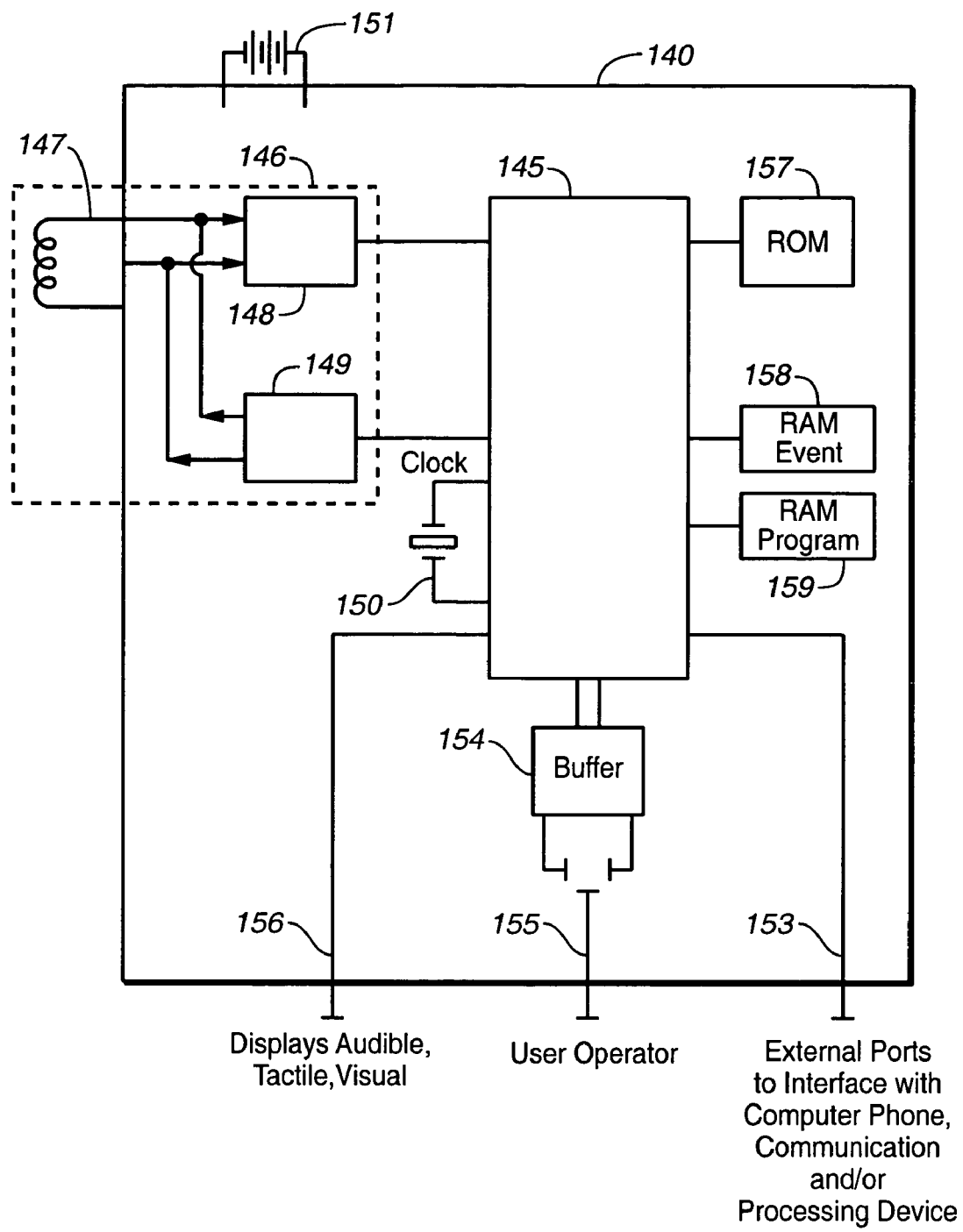
FIG._4

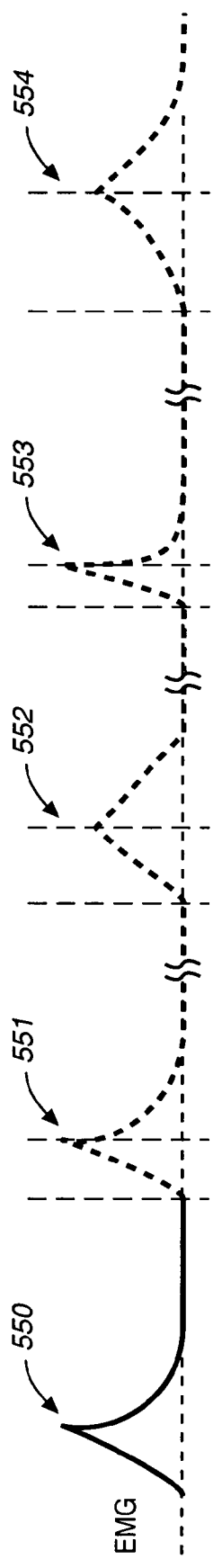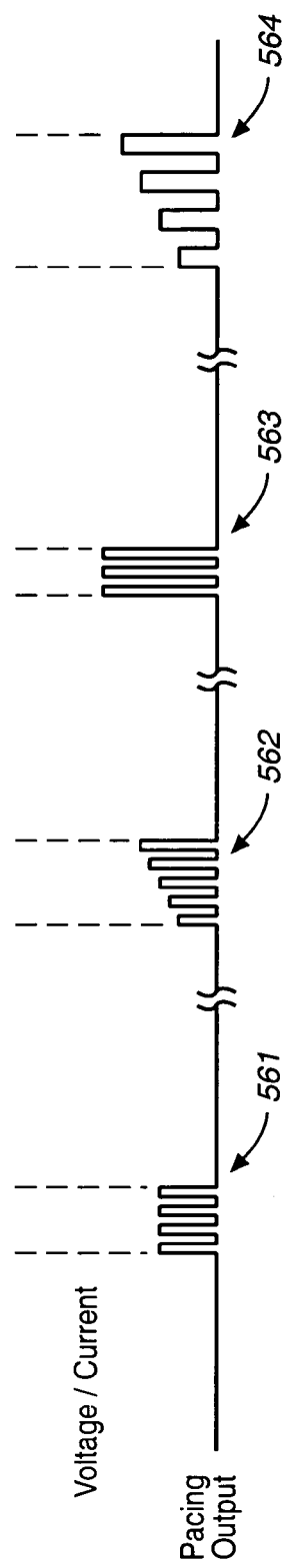

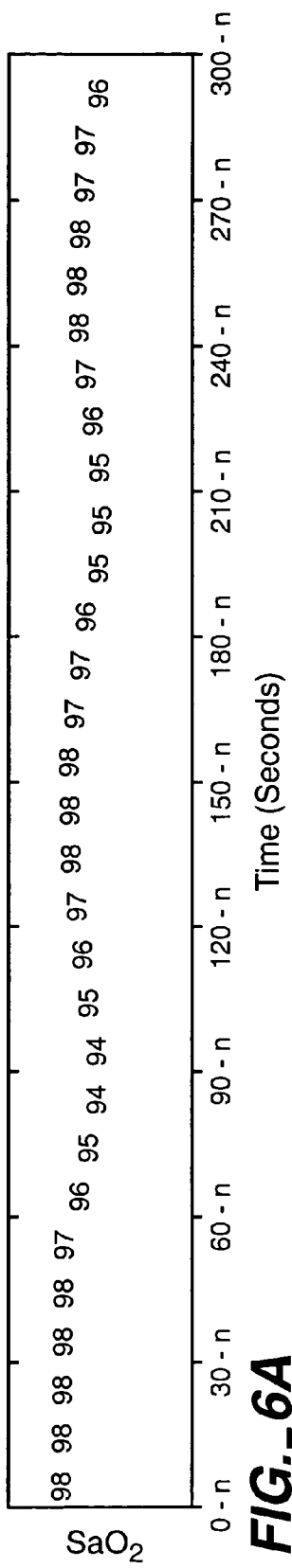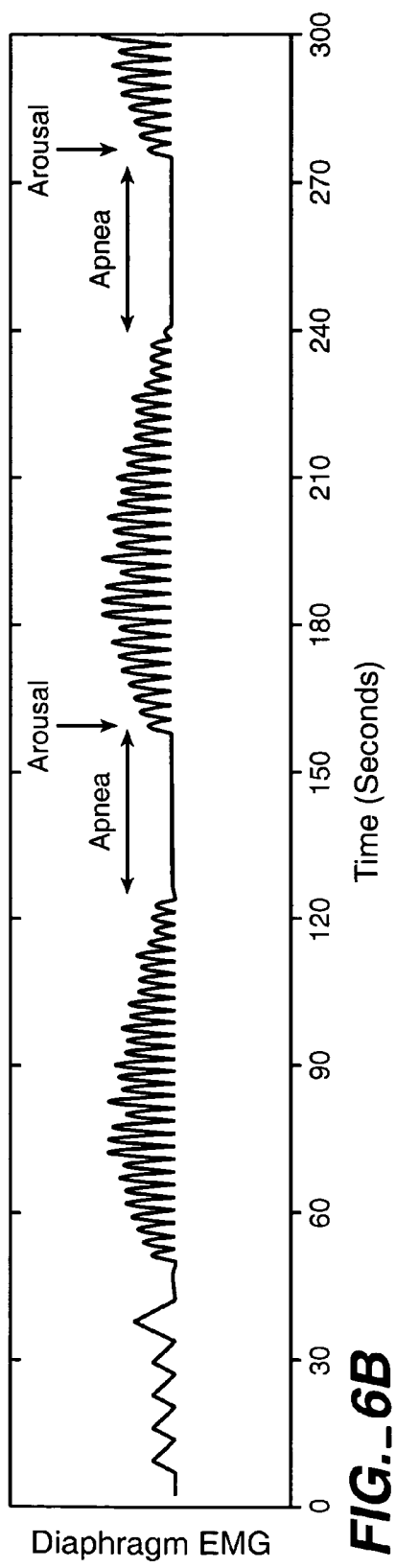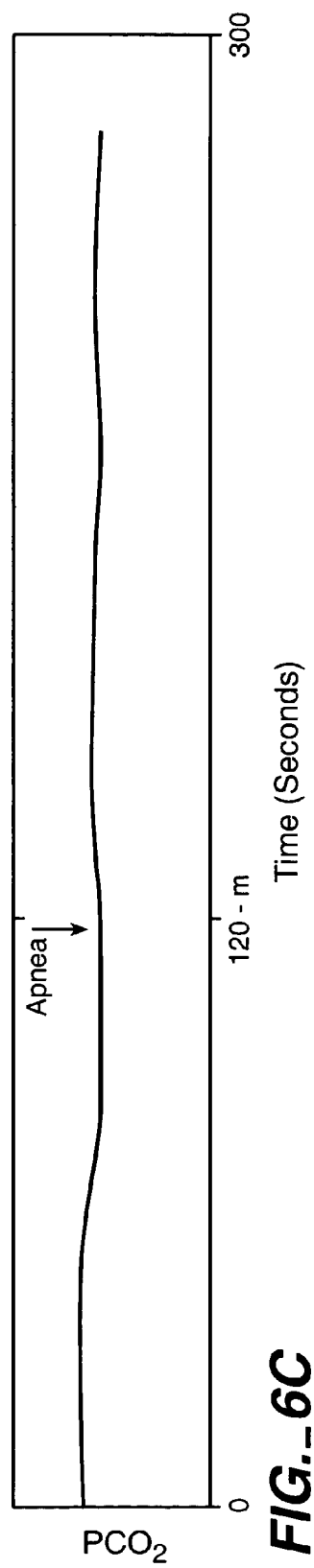

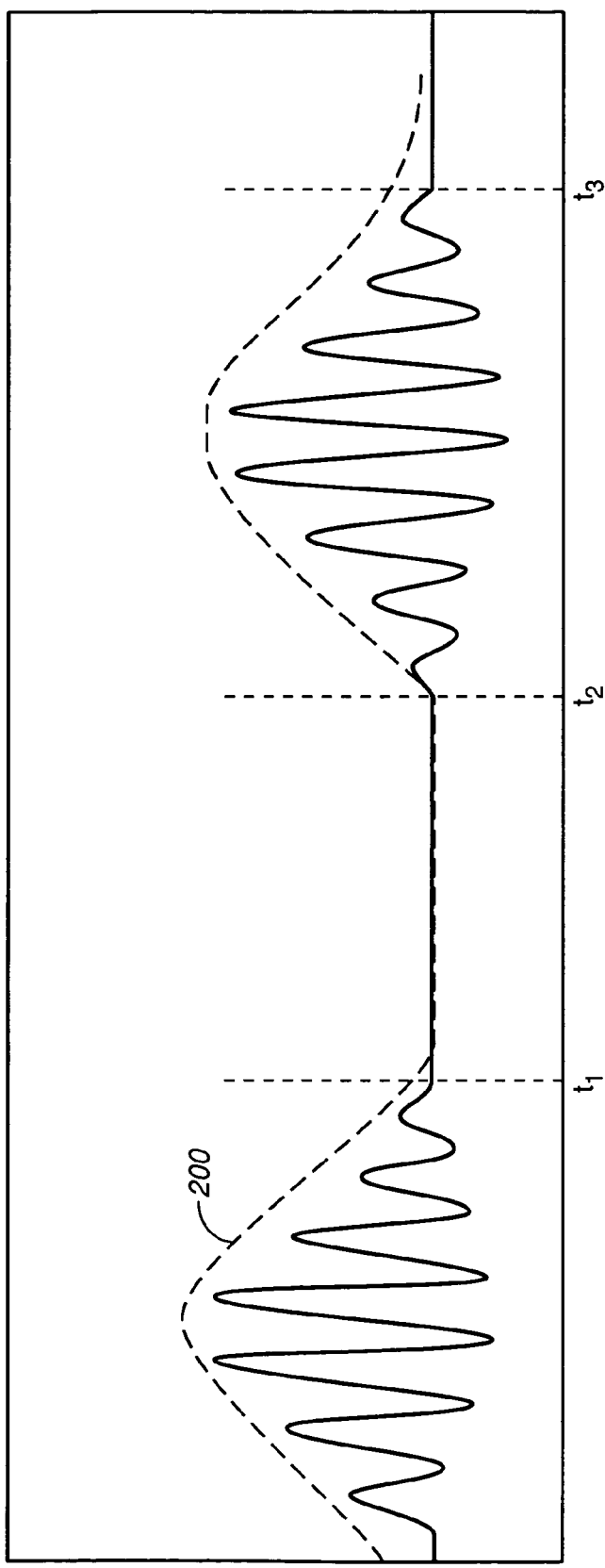
FIG._7
(PRIOR ART)

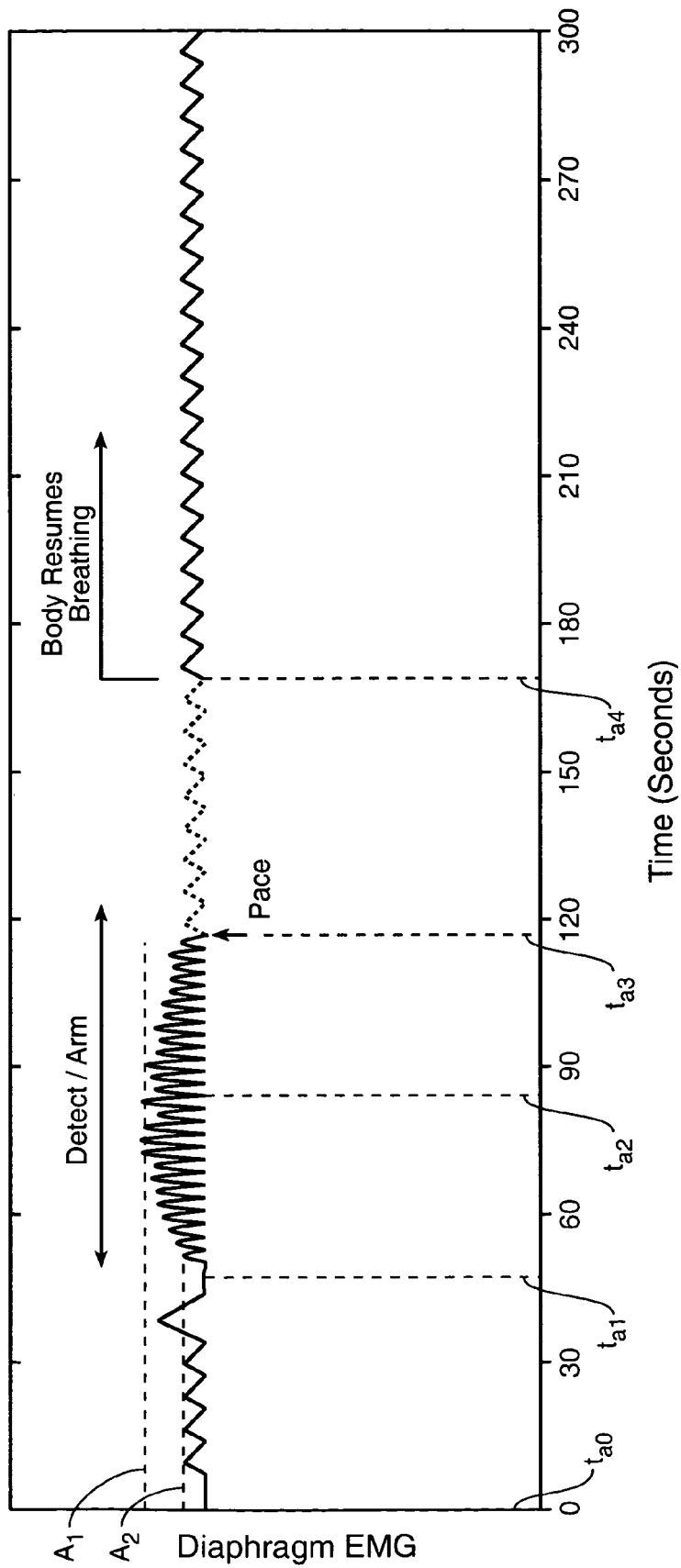
FIG._8

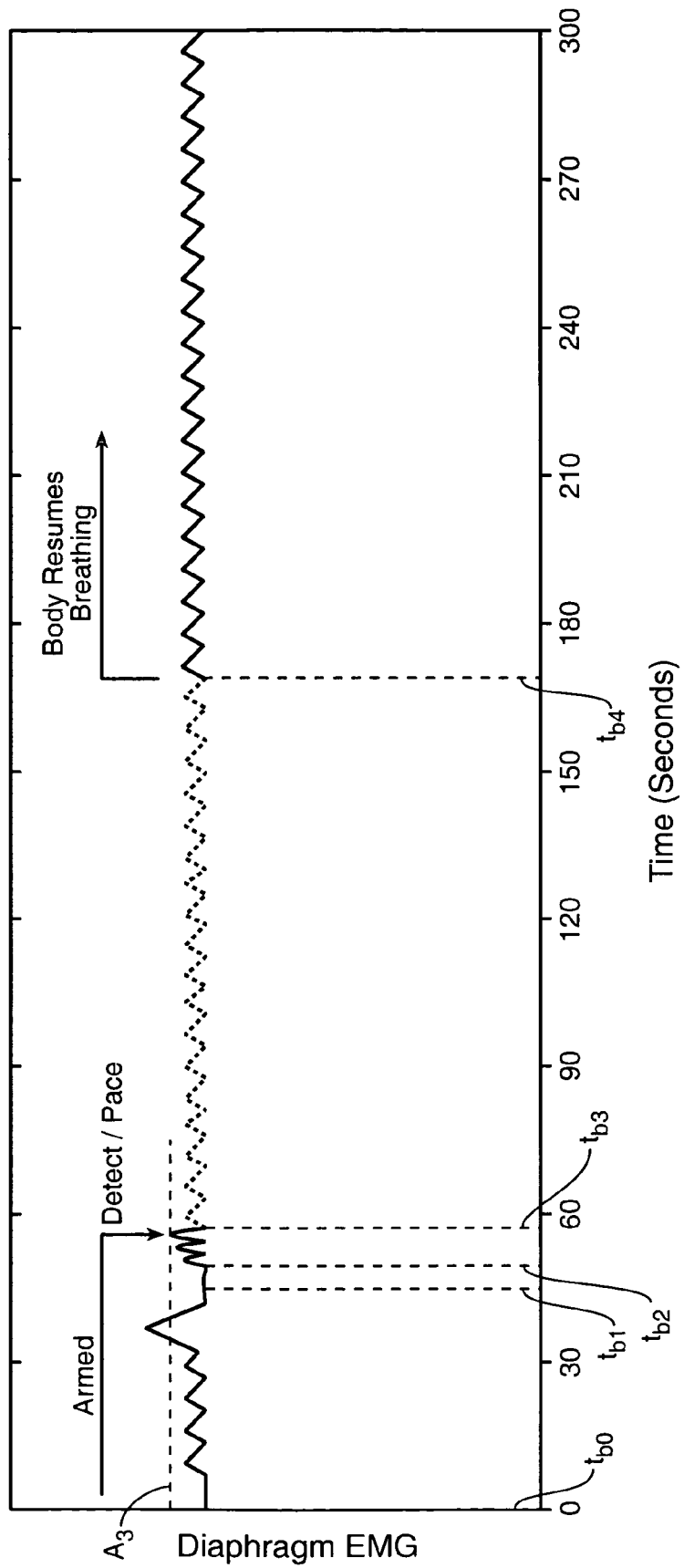
FIG._9

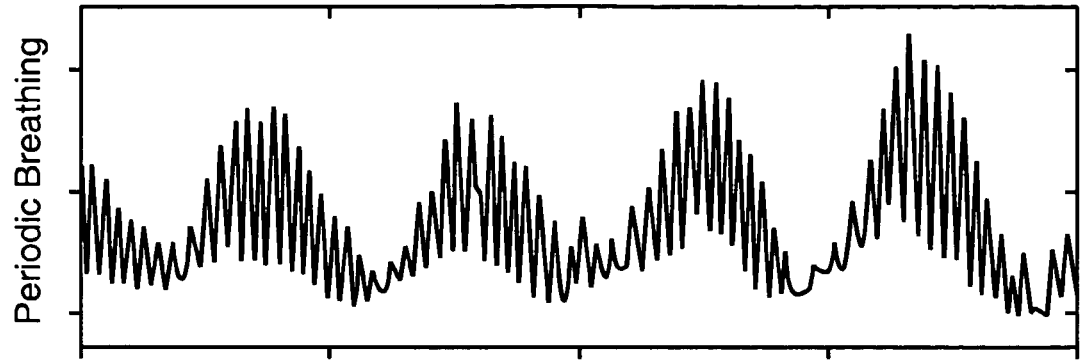
FIG._10A
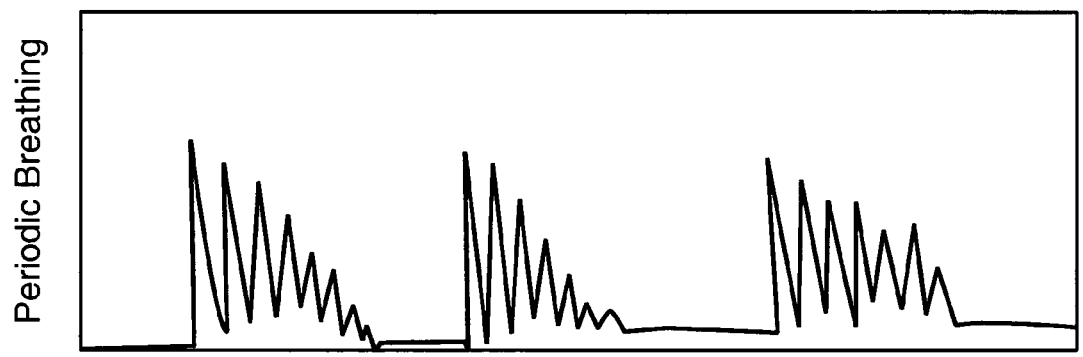
FIG._10B

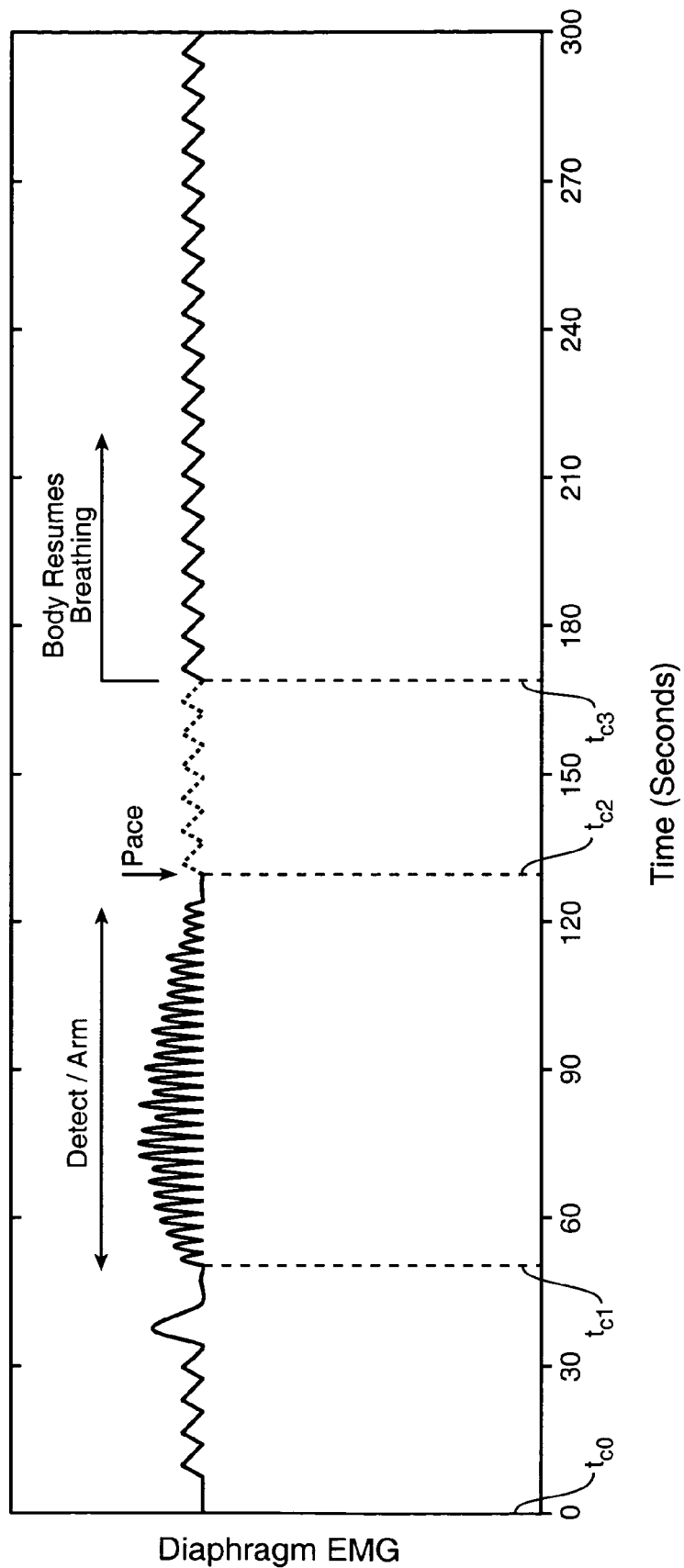
FIG._11

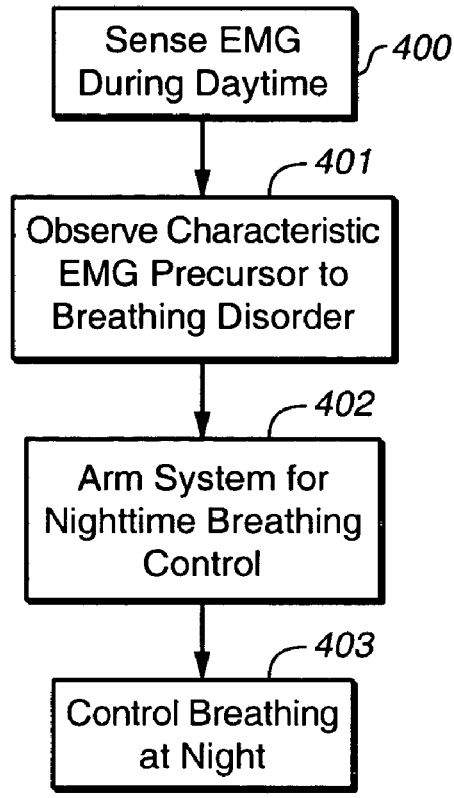
FIG._12
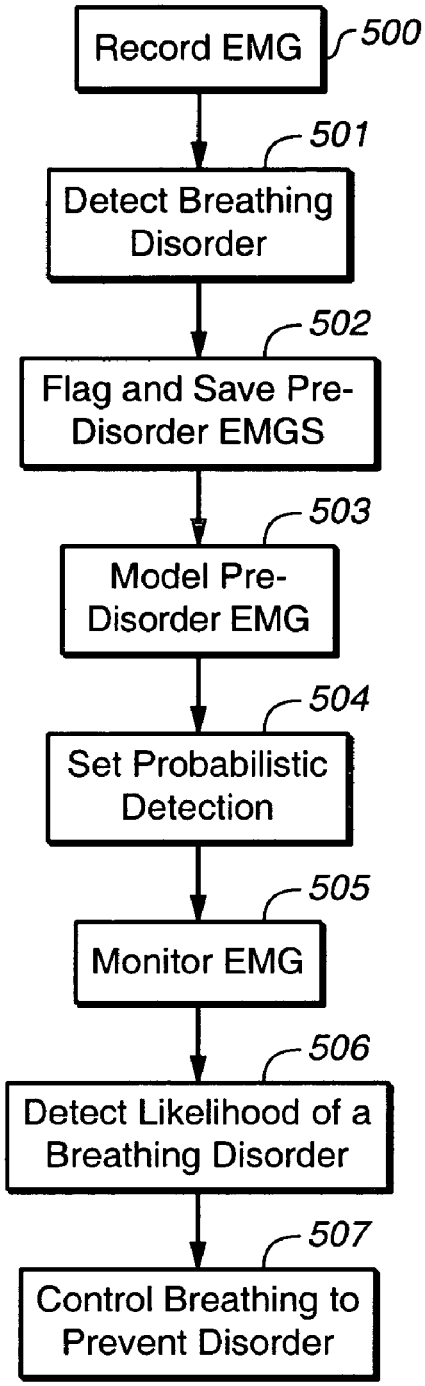
FIG._13

BREATHING DISORDER AND PRECURSOR PREDICTOR AND THERAPY DELIVERY DEVICE AND METHOD

RELATED APPLICATION DATA

This application is a continuation-in-part of U.S. application Ser. No. 10/686,891 filed Oct. 15, 2003, fully incorporated herein by reference.

FIELD OF THE INVENTION

The invention relates to a device and method for detection, diagnosis and treatment of breathing disorders and to the management of pulmonary or cardiac rhythms. The invention further relates to treating breathing disorders in response to detecting and/or predicting at least one precursor of such breathing disorder. In particular the invention relates to preventing or reducing breathing disorders by detecting and/or predicting a precursor and treating a subject by controlling breathing in response to detecting or predicting the precursor. In addition the invention relates to treating cardiac related disorders by detecting a precursor to a breathing disorder and in response, controlling breathing.

BACKGROUND OF THE INVENTION

Breathing insufficiencies, irregularities and other disorders may occur in conjunction with or as a result of a variety health related disorders and may further cause or exacerbate health disorders.

Disordered breathing may contribute to a number of adverse cardiovascular outcomes such as hypertension, stroke, congestive heart failure, and myocardial infarction. Sleep-related breathing disorders, especially central sleep apnea, have been found to have a relatively high prevalence in patients with congestive heart failure and may have a causative or influencing effect on such heart failure. In about 50% of patients with stable congestive heart failure, there is an associated sleep disordered breathing, predominantly central sleep apnea, with a minority having obstructive sleep apnea. Furthermore, sleep related breathing disorders are believed to be physiologically linked with congestive heart failure. Central sleep apnea is a known risk factor for diminished life expectancy in patients who suffer from congestive heart failure. It is also believed that in view of this link, treatment aimed at relieving sleep related breathing disorders may improve cardiovascular outcomes in patients with congestive heart failure.

Pulmonary edema, a condition in which there is excess fluid in the lungs and often found in heart failure patients, is believed in some circumstances to lead to hyperventilation and hyperoxia or apnea. Most heart failure patients with central sleep apnea, when lying flat, tend to have central fluid accumulation and pulmonary congestion, which may stimulate vagal irritant receptors in the lungs to cause reflex hyperventilation.

Breathing disorders may include, for example, hyperventilation, hypoventilation, apnea, and other related breathing disorders. Hyperventilation, which results in hyperoxia, is a condition in which the respiratory rate is pathologically high or is above a desired rate. Hyperventilation may occur due to pulmonary edema or excess fluid built up in the lungs and may ultimately result in apnea episodes. Hypoventilation is a condition in which the respiratory rate is pathologically low or below a desired rate. Apnea (absence of breathing) is a breathing disorder most typically occurring during sleep that can result from a variety of conditions.

Sleep breathing disorders include two types of sleep apnea: obstructive sleep apnea (partial apnea or obstructive apnea) and central sleep apnea. Obstructive sleep apneas result from narrowing of the pharynx with out-of-phase breathing in an effort to create airflow, whereas central sleep apnea arises from reductions or other abnormalities in central respiratory drive. Partial apnea may be a condition in which central respiratory drive is reduced and in which there is an obstruction or narrowing of the airway. During obstructive sleep apnea, respiratory effort increases. Complete apnea or central apnea is defined as a condition where there is no effective EMG signal or phrenic nerve signal, i.e. where there is no effective or significant physiological response. In central sleep apnea, respiratory movements are absent or attenuated but in phase with normal breathing. Sleep apnea typically results in some sort of arousal or wakefulness following cessation of breathing.

Central Sleep Apneas usually are initiated by reduction in $PCO_2$ resulting from an increase in ventilation. When $PCO_2$ falls below the threshold level required to stimulate breathing, the central drive to respiratory muscles and airflow cease or diminish significantly and apnea (or attenuated breathing) ensues until the $PCO_2$ rises again above the threshold required to stimulate ventilation. Often spontaneous arousal occurs with apnea.

Prior to central sleep apnea and some partial apneas, a respiration pattern or breathing disorder called Cheyne-Stokes, frequently occurs. A Cheyne-Stokes respiration pattern of breathing is also frequently associated with congestive heart failure, pulmonary edema, as well as with both obstructive and central apneas. The Cheyne-Stokes respiration pattern comprises a cyclical and often repeating pattern of a period of hyperventilation typically followed by a period of apnea. The hyperventilation portion of a Cheyne-Stokes respiration pattern has a morphology of a gradually increasing breathing pattern in depth and frequency followed by a gradually decreasing pattern in depth and frequency. The period of characteristic hyperventilation is followed by a period of apnea or hypopnea. It is believed that the onset of Cheyne-Stokes in CHF and pulmonary edema patients is caused by low blood oxygen saturation ($SaO_2$) levels resulting from cardiac, pulmonary insufficiencies, or circulatory delay. The $SaO_2$ receptors associated with the carotid artery are believed to perceive a drop in $SaO_2$ where there is a time lag in receiving oxygenated blood due to cardiac insufficiencies.

To compensate for drop in $SaO_2$, hyperventilation typically ensues. And, after a period, this hyperventilation pattern increasing in depth and frequency, the $PCO_2$ levels begin to drop below the chemoreceptor threshold, resulting in apnea.

Currently a number of methods are used to treat sleep apnea. For example, supplemental oxygen supplied through a nasal ventilator has been used to relieve symptoms of sleep apnea. Non-invasive airway pressure including continuous positive airway pressure (CPAP), bivalve and adaptive pressure support servo-ventilation have been used to treat central sleep apnea and obstructive sleep apnea with varying results. Another method to treat central sleep apnea is using aggressive diuresis to lower cardiac filling and beta-blocker and angiotensin-converting enzymes. However, this treatment is often not optimal since excessive use of diuretics leads to renal complications and patient discomfort.

A method and apparatus for treatment of obstructive sleep apnea and central sleep apnea has been proposed where an implantable pulse generator stimulates a nerve in the upper airway tract of a patient and a stimulator stimulates the diaphragm. The upper airway tract stimulation opens the airway tract to permit breathing in response to detecting a pressure differential across the upper airway passage indicating obstructive sleep apnea. The diaphragm stimulation treats central sleep apnea in response to sensing central sleep apnea.

Phrenic nerve stimulation has been used to stimulate the diaphragm throughout an overnight period to treat patients with Central Congenital Hyperventilation at night. The device used was turned on at night to stimulate the nerve continuously and then turned off during the day. However, this device was not adapted for situations where patients would breathe spontaneously. It also does not adjust for a patient's varying needs during the night.

While some methods have been proposed to determine when sleep apnea has occurred and to attempt to induce breathing when apnea occurs, they do not prevent an apnea episode. They also do not predict an apnea episode and therefore can only deliver treatment based on sensed rather than predicted conditions or events.

U.S. Pat. No. 6,641,542 discloses a method and apparatus to detect and treat sleep respiratory events. A processor extracts an average cycle length and frequency of at least one of a Cheyne-Stokes respiration and periodic breathing based upon the physiological data, and determines whether therapy is required based on the average cycle length and the frequency. The specific therapy disclosed was either pacing the heart to increase the heart rate or stimulating the hypoglossal nerve to cause contralateral extension of the patient's tongue or an increase in volume of the patient's oropharynx in accordance with U.S. Pat. No. 5,591,216. While according to the disclosure, the severity of Cheyne-Stokes is used to determine whether or not to stimulate, it is not believed to be used to determine or predict the likelihood of an apnea event subsequently occurring.

Accordingly it would be desirable to provide a method and apparatus for to prevent a breathing disorder episode. It would also be desirable to provide a method an apparatus for identifying a likelihood of a disordered breathing episode occurring.

SUMMARY OF THE INVENTION

The present invention provides a method and apparatus for sensing a precursor to or predicting a likelihood of a breathing disorder event or episode. "Sensing" as used herein may include but is not limited to, sensing with a sensor and/or detecting or recognizing various parameters, breathing patterns, etc. The present invention further provides a device and method for treating a subject by controlling breathing to avoid or prevent the breathing disorder event after sensing a precursor or determining a likelihood of the breathing disorder. According to one variation, the breathing disorder event is apnea or the onset of an episode of apnea. According to another variation, the breathing disorder event is an episode of Cheyne-Stokes respiration. According to another aspect, a sensor senses a precursor and an analyzer recognizes a respiratory pattern corresponding to a likelihood of a subsequent breathing disorder occurrence. Analyzer as used herein may comprise software, hardware or a combination thereof.

The precursor may be one or more of several indicators of a possibility or likelihood of a breathing disorder event occurring in the near or foreseeable future. Such indicators may include a particular breathing pattern such as a periodic breathing pattern, hyperventilation or occurrence of a Cheyne-Stokes pattern of hyperventilation prior to an apnea event, or other breathing rhythm or pattern that leads to a disorder. Immediately preceding Cheyne-Stokes, in some patients, there is a long deep breath which may be detected as a precursor. The EMG waveform or diaphragm movement morphology, rate, and amplitude, for example may be used to identify a precursor breathing disorder pointing to an event.

A number of other indicators may be used as precursors whether occurring immediately or a longer time period before a breathing disorder event. Biochemical changes prior to breathing disorders may be detected. For example, sensed $SaO_2$ and $PCO_2$ levels in the blood change prior to a Cheyne-Stokes hyperventilation event, and prior to apnea respectively may be detected. The $SaO_2$ level drops due to insufficiencies of the heart's and/or lungs' functioning, which is believed to cause the initiation of Cheyne-Stokes respiration. The increased breathing in the Cheyne-Stokes leads to a drop in $PCO_2$ which is believed to cause the initiation of apnea. These changes in blood gas concentrations may be predictors or precursors of the breathing disorder of Cheyne-Stokes and apnea respectively.

In addition, heart rhythm may be monitored and certain patterns in heart rhythm may indicate or predict the onset of Cheyne-Stokes or of Apnea. For example, if the duration of a QRS (the series of deflections in an electrocardiogram that represent electrical activity generated by ventricular depolarization prior to contraction of the ventricles) interval is longer than a specified period for a particular patient (i.e. >120 ms), then there is a likelihood in cardiac output reduction further increasing probability of circulatory delay and resultant Cheyne-Stokes respiration. Changes in heart rate and detection of any arrhythmias may also be indicative of the heart condition further increasing the possibility of increased circulatory delay and thus, a resulting Cheyne-Stokes respiration.

In addition, a blood velocity monitor may be used to determine particular blood flow characteristics, for example, changes in cerebral blood flow velocity. Cerebral blood flow changes may be precursors related to changes in blood gas volume. For example, an increase or decrease in velocity may relate to a change in cardiac output.

Such breathing pattern or other precursors may be different on a per patient basis. For example, the device may sense, record and analyze a plurality of breathing sequences or other precursors that precede breathing disorder events for a particular individual. The device may then devise a predictive model based on the precursor breathing patterns to earlier breathing disorder events. Such model may include a determination of a likelihood of the next event occurring in a particular individual. For example, the device may monitor breathing for a plurality of consecutive nights to learn about the pattern and morphology of breathing prior to a disorder such as, e.g., Cheyne-Stokes or apnea.

In observing, recording and analyzing prior events, the device may observe precursors occurring a period of time prior to the event, e.g., seconds, or minutes before, or during a day before a breathing disorder event occurring at night. A baseline or normal level of one or more indicators may be identified. The device will record such indicator for a period of time prior to an event occurring. The baseline can be compared to a pre-event recorded indicator. A pattern is identified using predictive algorithms and digital signal processing techniques. Future indicators are then observed and compared to a predictive model or pattern to determine the likelihood or probability of an event occurring in the future. Such detection may also include, for example, tracking or counting episodes or frequency of episode occurrence to determine a likelihood of an event occurring. The frequency and number of events during a daytime period may also be used to calculate a likelihood of a breathing disorder occurring during a nighttime period. A percentage of time in which disordered or periodic breathing occurs may also be used as a threshold for predicting a later occurring breathing disorder. The predictive model may also be determined on a patient by patient basis. The apnea event or other breathing disorder has a likelihood of following a precursor but does not always follow.

A precursor may be an event, a series of events or patterns of events, existence of a condition, a series of conditions or a pattern of conditions that precede an apnea event or other breathing disorder, and that indicate a likelihood of an apnea event or other breathing disorder, occurring. A combination of the precursors described above may be used to make a likelihood determination.

As an example of a precursor, rapid, periodic, or shallow breathing during the day when there is no corresponding increase in activity level indicates a possibility of a nighttime breathing disorder occurring. A low activity level in combination with a higher rate of breathing provides information regarding the status of a patient's pulmonary edema. This information can be correlated to a likelihood or possibility of sleep disordered breathing occurring during the night (e.g. Cheyne-Stokes respiration or sleep apnea). Alternatively, a patient's edema status, where severe, may be used to turn off stimulation if such stimulation is believed to be ineffective under the circumstances.

A precursor may also be an event or condition that usually occurs prior to a Cheyne-Stokes event and particularly in congestive heart failure patient. Such precursor may be, for example, a decrease in $SaO_2$ or a particular heart rate, blood pressure, blood velocity or a particular breathing pattern or morphology as determined, e.g., by an EMG of the diaphragm. The device or method may comprise a detector configured to detect a portion or a characteristic of such Cheyne-Stokes pattern of hyperventilation. Cheyne-Stokes may be detected by detecting sensing and or analyzing a portion of a Cheyne-Stokes respiration pattern. The general envelope or portion of an envelope of such pattern may be detected. Increasing or decreasing hyperventilation amplitude and/or frequency may also be used to detect Cheyne-Stokes hyperventilation.

In addition when hyperventilation occurs, there may be a threshold peak amplitude that is detected above which apnea most likely will occur. When this amplitude is detected, stimulation is provided to control breathing. The threshold may be determined on a patient by patient basis by observing peak values of hyperventilation and the subsequent occurrence of apnea. Also a peak may be identified as a predetermined percentage of a baseline breathing amplitude.

One aspect of the invention provides a responsive device configured to treat a subject prior to the occurrence of a likely breathing disorder or to avoid or reduce symptoms of a breathing disorder. In response to identifying a precursor, the treatment, for example, may comprise controlling breathing by electrically stimulating the phrenic nerve or diaphragm to control breathing. Breathing rate or inspiration morphology may be controlled to avoid or reduce the breathing disorder episode. For example, breathing may be stimulated to influence or manipulate $PCO_2$ and maintain $SaO_2$ levels, for example, by causing shallow and long inspiratory cycles. Examples of influencing $PCO_2$ and $SaO_2$ are described in copending application entitled: "*System And Method For Diaphragm Stimulation*" incorporated herein by reference.

The stimulation scheme of the invention may be used in a number of applications. In general, a patient's breathing is captured by the stimulator and breathing stimulation is applied to control breathing for a period of time.

According to one aspect of the invention, stimulation is provided that inhibits central respiratory drive for a sufficient duration so that therapeutic stimulation and breathing control may be applied. The therapeutic stimulation breathing is configured to provide a therapeutic benefit at the same time that it acts to inhibit central respiratory drive.

A time period may be identified for stimulating a diaphragm and/or phrenic nerve to elicit a breathing response where the stimulation is believed to capture or take over breathing control and/or inhibit breathing driven by a subject's innate respiratory drive.

In addition stimulation may also be provided during an exhalation cycle to further extend the length of the active breathing portion (inspiration and exhalation) of the respiration cycle. The duration of the rest period is greatly reduced so that the central respiratory drive may remain inhibited.

The increase in the duration of the active breathing portion of the respiration cycle decreases the rest phase duration which tends to inhibit the occurrence of spontaneous breathing.

Parameters that effect minute ventilation e.g., tidal volume and respiratory rate, may be manipulated to control respiratory drive.

In one application, breathing is stimulated to increase oxygen saturation levels for a period of time. The oxygen saturation levels can be increased by increasing minute ventilation.

Another aspect of the invention provides for breathing therapy in treating apnea. It is believed that stimulated breathing prior to or during apnea may stabilize the broad swings of blood gas concentrations that occur during cycles of Cheyne-Stokes and apnea. Further it is believed that diaphragmatic stimulation during apnea may stimulate vagal afferent signals to the respiratory center and thus may maintain vagal tone associated with restful sleeping. Vagal tone has a calming effect on heart rate, blood pressure and cardiac output during restful sleep stages. Furthermore, diaphragmatic stimulation may prevent a fall in oxygen saturation that would typically initiate an arousal episode during apnea. Arousal episodes are associated with increases of sympathetic nerve activity which increases ventilation rate, heart rate and blood pressure. If oxygen saturation falls below a threshold, it is believed that hyperventilation will attempt to compensate for the falling oxygen saturation and also create arousal. Accordingly the invention provides a device and method for preventing apnea arousals. The invention also provides a device and method for providing greater periods of restful sleep particularly in patients suffering from ongoing bouts of apnea and resulting arousal from sleep.

The stimulation may be adjusted to increase or decrease minute ventilation to stabilize blood gas fluctuations and avoid further episodes of Cheyne-Stokes and/or apnea. Maintaining stable blood gas levels with stimulation may prevent Cheyne-Stokes hyperventilation and hence avoid arousal events otherwise associated with large swings of these gases.

In one variation, the device will sense or recognize when an event is about to occur and will take over control of breathing and thereby prevent the onset of the breathing disorder. For example, when predicting a disorder and/or after sensing or recognizing a hyperventilation portion of the Cheyne-Stokes respiration pattern, a breathing stimulation is initiated to control and regulate breathing and to interrupt the hyperventilation pattern. For example, stimulation to control breathing and increase $SaO_2$ may be initiated upon detecting the first few breaths of a Cheyne-Stokes hyperventilation. Alternatively, stimulation to control breathing and increase $PCO_2$ may be initiated upon detecting the end of the envelope or patterns of a Cheyne-Stokes hyperventilation event. As such, the stimulation may prevent the apnea from occurring.

The response to sensing a precursor prior to an event, may be to arm a device so that a disorder recognizing device is on a higher level of alert for recognizing a breathing disorder or for sensing another precursor. A responsive device may adjust the sensitivity of an apnea or other breathing disorder monitor when the likelihood of an event occurring changes.

Certain sensing, detection or analysis functions or sensors may be enabled, or armed when a likelihood of an event occurring is determined. For example, where certain precursors were sensed during the daytime period, the system may be armed for the following nighttime period. Alternatively, the device may just take over breathing to prevent any disorder after it has been determined that a sufficient likelihood exists for a breathing disorder to occur. For example, the device may determine a likelihood of an event occurring based on events during the daytime. In response to the likelihood exceeding a predetermined threshold, the device will control breathing at night, either continuously or on an intermittent basis.

The method and apparatus provide stimulation to the diaphragm to elicit diaphragm movement or to an associated body organ or tissue to control movement of the diaphragm and thus manage or control respiration when desired. Alternatively, the phrenic nerve may be directly accessed and stimulated.

One embodiment is a device comprising: one or more sensors (e.g. EMG, ECG, diaphragm movement, or activity sensors, blood gas sensors, blood pressure sensors, blood velocity sensors) for sensing information corresponding to respiration of the diaphragm and/or a precursor to a breathing disorder. A processor is provided for processing the sensed information to identify a precursor, and delivering electrical stimulating pulses to the associated body organ or tissue to control breathing or prevent occurrence of an episode of a breathing disorder. The processor may further determine stimulation parameters or time the stimulation response based at least in part on sensed information. A number of different parameters may be programmed into the processor to determine when and how to stimulate respiration based at least in part on presence or absence of a detected precursor. Other information may also be sensed and used to determine if to stimulate, and when to stop or modify stimulation. Also, the processor may determine when to cease stimulation by determining when the body resumes normal respiratory function, when respiration has been captured or is being controlled by the stimulation, or when the breathing disorder has been prevented or treated.

The respiratory effort or respiration may be sensed, for example, by sensing the phrenic nerve activity and/or the EMG of the diaphragm, or by detecting movement of the diaphragm or chest. Respiration by the diaphragm may be stimulated by electrically stimulating the phrenic nerve and/or by stimulating the diaphragm muscle.

Phrenic nerve or EMG activity sensed may include, for example, amplitude, frequency, and waveform to determine central respiratory efforts, the absence, a decrease in amplitude, abnormalities in frequency and/or amplitude, or waveform morphology of which may indicate a likelihood of the onset of apnea, hyperventilation, or hypoventilation or other breathing disorders. The nerve activity may be compared to predetermined activity levels or patient historical activity. A period of abnormal activity or similar pattern during an earlier period may be used to determine the likelihood of sleep apnea occurring later during sleep.

An awake sinus zone may be defined as a respiratory rate or range of rates or patterns programmed into the device for a specific patient when awake, where the respiratory rate is considered normal and intrinsic. A preprogrammed EMG amplitude or range may define a normal range or pattern in this state. An abnormal pattern type may also be programmed in for use in detecting a precursor breathing pattern. Such patterns may be observed by a device and saved in memory and used to detect when a similar precursor pattern occurs. Or, such patterns may be preprogrammed in the device for recognition. A sleep sinus may be defined as a respiratory rate or range of rates or pattern programmed into the device for a specific patient when asleep where the respiratory rate or pattern is considered normal and intrinsic. A preprogrammed EMG amplitude or range may define a normal range in this state. The device may be programmed to match the EMG rate and amplitude when stimulating to a normal rate and amplitude by auto adjusting the pace output.

In addition, position sensors may be used to determine degree of patient reclining or standing, e.g., in increments of degrees. Information from the position sensor may be used as a tool to match respiratory activities and patterns to the position of the patient. Accelerometer information may be used to determine information regarding patient's physical activity, e.g., to match/compare to the respiratory patterns and activities and collect data on related patient activities, respiratory activities.

Alternatively or in addition, accelerometer sensors may also be used to determine information regarding movement pattern of the diaphragm muscles, intercostal muscles, and rib movement and thus determine overall respiratory activity and patterns. These sensors may also be used to observe response to stimulation.

According to an embodiment, a stimulator includes an implantable controller coupled through leads to electrodes to be implanted on the diaphragm in the vicinity of the phrenic nerve branches. The electrodes may sense either nerve activity or EMG signals of the diaphragm. The stimulator may further include a pulse generator configured to deliver stimulating pulses, either to the same electrodes used for sensing or to additional stimulation electrodes. The stimulation electrodes may also be placed adjacent the phrenic nerve at some point along its length to provide stimulation pulse to the nerves, which in turn innervate the diaphragm muscle causing contractions and resulting respiration. Alternatively the electrodes may be placed on the phrenic nerve for both sensing and stimulation.

Stimulation of respiration may be initiated during a detected precursor event or at a given time after detection of onset of the precursor event. The time period may be preprogrammed for a specific patient by the physician, as otherwise preset, or as determined a program in the treatment device.

Breathing stimulation may start at given intervals. In one embodiment the interval time is initially about 10 seconds. The interval is slowly increased from 11 seconds to about 15 seconds. If breathing is brought back within a normal range, the stimulation may be terminated until another precursor is detected. If breathing is not controlled as desired, the pacing begins again at 10-second intervals and this is repeated (loop). Alternatively the stimulator may be held at the longest duration of the cycle until breathing resumes (hold). If the patient's breathing is normalized and they are breathing on their own, typically where the $SaO_2$ and $PCO_2$ levels are normalized and the brain resumes sending nerve stimulation. The system then returns to the mode where it is sensing to detect a precursor. Alternatively the stimulator may be turned on for a set period of time where a likelihood exists for an occurrence of a breathing disorder. After the period of time, the progressively increasing periods (hysteresis) between stimulation may be made until intrinsic breathing resumes with a loop or hold pattern.

An additional feature of the invention may include a patient self-management module configured to communicate with the patient or provider. Such module is described, for example, in application Ser. No. 10/686,891 entitled "Breathing Disorder Detection and Therapy Delivery Device and Method" incorporated in its entirety herein by reference.

This device may also measure and monitor heart rate and activity by sensing ECG. This information may be used to provide breathing stimulation to induce desired breathing patters to reduce the clinical impact of an abnormal heart function. If a patient is a CHF patient or suffers other heart disease, breathing can be controlled to increase $SaO_2$ thereby reducing the load on the heart (e.g., reducing heart rate and pumping activity and consequently myocardial contractibility). Reducing the load can lead to positive remodeling of the myocardium.

DETAILED DESCRIPTION OF THE DRAWINGS

FIG. 1 is a schematic of a sleep breathing and heart disorder treatment device in accordance with the invention placed on the diaphragm.

FIG. 2 illustrates a processor unit of a sleep breathing and heart disorder treatment device in accordance with the invention.

FIG. 3A is a schematic of a signal processor of the processor unit in accordance with the invention.

FIG. 3B is an example of a waveform of an integrated signal processed by the signal processor of FIG. 3A.

FIG. 4 is a schematic of an external device of a stimulator in accordance with the invention.

FIGS. 5A-5B are an illustration of a variety of stimulation bursts with different parameters (FIG. 6B) corresponding to different resulting EMG signals.

FIG. 6A is an exemplary graph of $SaO_2$ values as precursors to or during breathing disorder episodes as shown in FIG. 6B.

FIG. 6B is an exemplary graph of diaphragm EMG prior to and during a Cheyne-Stokes hyperventilation episode and prior to, during and subsequent to apnea episodes.

FIG. 6C is an exemplary graph of $PCO_2$ values corresponding to the diaphragm EMG illustrated in FIG. 6B.

FIG. 7 is a schematic of a Cheyne-Stokes breathing pattern.

FIG. 8 is an exemplary graph of a precursor detection and treatment response in accordance with the invention.

FIG. 9 is an exemplary graph of a precursor detection and treatment response in accordance with the invention.

FIGS. 10A and 10B is an exemplary graphs of various exemplary breathing disorder precursor patterns.

FIG. 11 is an exemplary graph of a Cheyne-Stokes detection and treatment response in accordance with the invention.

FIG. 12 is a precursor detection and treatment scheme in accordance with the invention.

FIG. 13 is a precursor detection and treatment scheme in accordance with the invention.

DETAILED DESCRIPTION OF THE INVENTION

FIG. 1 illustrates a stimulator 20 comprising electrode assemblies 21, 22, each comprising a plurality of electrodes 21a-d and 22a-d respectively. The electrode assemblies 21, 22 are implanted on or in the diaphragm muscle so that one or more of electrodes 21a-d and of electrodes 22a-d are approximately adjacent to one or more junctions of the phrenic nerves 15, 16, respectively, with the diaphragm 18 muscle. Mapping techniques for identifying optimal electrode placement is described in contemporaneously filed application entitled "System And Method For Mapping Diaphragm Electrode Sites", fully incorporated herein by reference. The electrode assemblies may be in a variety of configurations including loops or other flexible configurations, including but not limited to, those described in parent application Ser. No. 10/686, 891, incorporated herein by reference.

The electrode assemblies 21, 22 sense and stimulate at the diaphragm muscle. They may sense diaphragm movement with movement sensors (e.g. with movement detectors 25, 26) and may also sense EMG and ECG. They are implanted laparoscopically through the abdomen and on the surface of the diaphragm or into the muscle of the diaphragm 18 with needles or other similar devices. The electrode assemblies 21, 22 may be anchored with sutures, staples, or other anchoring mechanisms typically used with implantable EMG electrodes. The leads 23, 24 coupling the electrode assemblies 21, 22 to the control unit 100 are then routed subcutaneously to the side of the abdomen where a subcutaneous pocket is created for the control unit 100. The electrode assemblies 21, 22 are each flexible members with electrodes 21a-d, assembled about 5-20 mm apart from one another and electrodes 22a-d assembled about 5-20 mm apart from one another. Any number of desired electrodes may be used on the assemblies 21, 22. The electrode assemblies 21, 22 are coupled via leads 23, 24 to control unit 100. The control unit 100 is configured to receive and process signals corresponding to sensed nerve activity, and/or EMG of the diaphragm 18, to determine the respiratory parameters and/or patterns of the diaphragm 18 as described in more detail herein. The control unit is also configured to process the sensed signal to determine ECG information. The electrodes assemblies 21, 22 are coupled via leads 23, 24 to input/output terminals 101, 102 of a control unit 100. The leads 23, 24 comprise a plurality of electrical connectors and corresponding lead wires, each coupled individually to one of the electrodes 21a-d, 22a-d. The control unit 100 is implanted subcutaneously within the patient, for example in the chest or abdominal region on top of the pectoral muscle (depending on the position of the electrodes, e.g. on the diaphragm or elsewhere along phrenic nerve). The control unit 100 is configured to receive sensed nerve electrical activity from the electrode assemblies 21, 22, corresponding to respiratory effort of a patient. The control unit 100 includes a processor 105 (FIG. 2) that delivers stimulation to the nerves 15,16 or diaphragm 18 in response to a sensed precursor effort as determined and processed by the processor 105 and control unit 100.

The stimulator 20 also comprises movement detectors 25, 26, included with the electrode assemblies 21, 22 respectively and electrically connected through leads 23, 24 to the control unit 100. A number of different movement detectors may be used, for example an accelerometer, strain gauges, piezo electric devices, and variable resistive devices. They may be coupled or in communication with the control unit 100 (or alternatively, the external device 140). The movement detectors 25, 26 detect movement of the diaphragm 18 and thus the respiratory effort exerted by the diaphragm 18, the respiratory waveform, respiratory rate or other respiratory parameters. The movement detectors 25, 26 sense mechanical movement and deliver a corresponding electrical signal to the control unit 100 where the information is processed by the processor 105. The movement may be used to qualify the electrical phrenic nerve or EMG signal sensed by the device to confirm inspiration or exhalation is occurring, e.g., by matching mechanical and electrical activities of the diaphragm. Movement may be used in a variety of ways to provide information on the condition of a patient. For example, it may be used as feedback system to mimic natural diaphragm movement when stimulating or as part of auto-adjustable therapy.

Another sensor 29 may be implanted in, attached or coupled to the body in a direct or indirect communication with the control unit 100 or external device 140, e.g. telemetrically or through lead wires. The sensor 29 may include one or more sensors positioned at one or more locations and used to sense information relating to precursors to breathing disorders. Such sensor(s) may include, for example, $SaO_2$ or $PCO_2$ blood gas monitors, heart rate monitors, blood velocity monitors or blood pressure monitors. An ECG sensor may be included as well. For example, ECG information may be filtered out of a signal from electrodes 21, 22.

The movement detectors or other sensors may be positioned on the electrode assembly, may be separately positioned on the diaphragm or elsewhere in or on the body. The movement sensor on the lead positioned on the diaphragm may monitor diaphragm movement as well as other movement information. The movement sensor located inside the electronics housing may be used to monitor patient activity as well as other movement information.

Electrodes may be selected from the plurality of electrodes 21a-d and 22a-d once implanted, to form electrode pairs or groups that optimize the stimulation response. They may also form selectable monopolar stimulation electrodes with a remote return electrode. Such desired response may include tidal volume, breathing rate and the slopes of the inhalation and exhalation curves. For example, a timed series of pulses may be used to create a desired respiratory inhalation and/or exhalation period. Optimal electrode location may be identified using a mapping system as described in copending application entitled "System And Method For Mapping Diaphragm Electrode Sites" filed on even date herewith and incorporated herein by reference. Alternatively, electrodes may be selected as described in the U.S. application Ser. No. 10/686,891.

As an alternative to placing electrodes on the diaphragm, sensing and/or stimulating electrodes may be placed on the phrenic nerve, for example at a location in the neck or thorax or at a combination of various locations.

FIG. 2 illustrates an implantable control unit 100. The control unit 100 includes electronic circuitry capable of generating and/or delivering electrical stimulation pulses to the electrodes of electrode assemblies 21, 22, through leads 23, 24, to cause a diaphragm respiratory response in the patient. For purposes of illustration, in FIG. 2, the control unit 100 is shown coupled through leads 23, 24 to electrode assemblies 21, 22 respectively. Electrodes from electrode assemblies 21, 22 may also act to sense EMG and thus respiration parameters. As such they may be used periodically as breathing characteristically occurring prior to breathing disorder or to sense a precursor, e.g. a breathing pattern such as periodic breathing characteristically occurring prior to a breathing disorder, or hyperventilation portion of a Cheyne-Stokes respiration. The electrode assemblies may also sense ECG signals which may be processed using known signal processing techniques.

FIG. 2 illustrates an implantable control unit 100. The control unit 100 includes electronic circuitry capable of generating and/or delivering electrical stimulation pulses to the electrodes of electrode assemblies 21, 22, through leads 23, 24, to cause a diaphragm respiratory response in the patient. For purposes of illustration, in FIG. 2, the control unit 100 is shown coupled through leads 23, 24 to electrode assemblies 21, 22 respectively. Electrodes from electrode assemblies 21, 22 may also act to sense EMG and thus respiration parameters. As such they may be used periodically as breathing characteristically occurring prior to breathing disorder or to sense a precursor, e.g. a breathing pattern such as periodic breathing characteristically occurring prior to a breathing disorder, or hyperventilation portion of a Cheyne-Stokes respiration.

The electrode assemblies may also sense ECG signals which may be processed using known signal processing techniques.

The control unit 100 comprises a processor 105 for controlling the operations of the control unit 100. The processor 105 and other electrical components of the control unit are coordinated by an internal clock 110 and a power source 111, such as, for example, a battery source or an inductive coupling component configured to receive power from an inductively coupled external power source. The processor 105 is coupled to a telemetry circuit 106 that includes a telemetry coil 107, a receiver circuit 108 for receiving and processing a telemetry signal that is converted to a digital signal and communicated to the processor 105, and a transmitter circuit 109 for processing and delivering a signal from the processor 105 to the telemetry coil 107. The telemetry coil 107 is an RF coil or alternatively may be a magnetic coil. The telemetry circuit 106 is configured to receive externally transmitted signals, e.g., containing programming or other instructions or information, programmed stimulation rates and pulse widths, electrode configurations, and other device performance or function details. The telemetry circuit 106 may also receive sensed information transmitted from sensor 29 which may also include a telemetry circuit. The telemetry circuit is also configured to transmit telemetry signals that may contain, e.g., modulated sensed and/or accumulated data such as sensed EMG or ECG activity, sensed nerve activity, sensed responses to stimulation, sensed position information, sensed movement information, sensed blood gas information, sensed blood velocity or pressure information, and episode counts or recordings.

The leads 23, 24 are coupled to inputs 101, 102 respectively, of the control unit 100, with each lead 23, 24 comprising a plurality of electrical conductors each corresponding to one of the electrodes or sensors (e.g., strain gauge) of the electrode assemblies 23, 24. Thus the inputs 101, 102 comprise a plurality of inputs, each input corresponding to one of the electrodes or sensors. The signals sensed by the electrode assemblies 21, 22 are input into the control unit 100 through the inputs 101, 102. Each of the inputs are coupled to a separate input of a signal processing circuit 116 (schematically illustrated in FIG. 2 as one input) where the signals are then amplified, filtered, and further processed, and where processed data is converted into a digital signal and input into the processor 105. Each signal from each input is separately processed in the signal processing circuit 116. The signal processing circuit 116 is coupled to the processor 105 which receives input from the signal processor 116. The processor processes the data in accordance with a program in RAM 120 and other stored data in RAM 119 to identify or detect a precursor breathing pattern or patterns. In response to such determination according to a program stored in RAM 120, the processor 105 controls stimulation of the diaphragm through electrode assemblies 21, 22.

The EMG/Phrenic nerve sensing has a dual channel sensor. One corresponding to each lung/diaphragm side. However, sensing can be accomplished using a single channel as the brain sends signals to the right and left diaphragm simultaneously. Alternatively, the EMG or phrenic nerve collective may be sensed using a single channel. Either a dual channel or single channel setting may be used and programmed. The typical pulse width parameter will range from 0.5 ms to 10 ms in increments of 50 μs. The pulse amplitude is from about 0.1 v to 5 volts in increments of 100 μV if the stimulation source is a voltage source. If the stimulation source is the constant current source, the stimulation intensity's range is about 1 mA-24 mA in increments of 0.5 mA, monophasic or biphasic waveforms, and pulse width(s) of about 50-200 microseconds. The amplitude and frequency may vary pulse by pulse within the same burst of pulses for a single inspiration waveform. The refractory period is 1 to 10 seconds in increments of 1 second. The system may adjust the pace, pulse, frequency and amplitude to induce or control rate of the various portions of a respiratory cycle, e.g. slope of inspiration, inspiration depth, inspiration length and tidal volume. The system may also adjust the rate of the respiratory cycle.

The system EMG & ECG memory is programmable to pre-trigger and post trigger lengths of storage for sleep apnea or other breathing disorder episodes. The pre-trigger events are the waveform signals and other sensed information observed prior to or in transitioning to an event. Post-trigger events are the waveforms and other sensed information observed after an event and/or after treatment following precursor detection, to observe how the device operated. Post-trigger recordings can confirm if the episode was successfully treated. The pre-trigger and post-trigger time periods can be preprogrammed into the control unit 100. Pretrigger events may be used in subsequent cycles as precursors for identifying a breathing disorder event likelihood.

The control unit 100 includes a position sensor 121 configured to sense a relative position of the patient, e.g. angular position, and provide a digital signal corresponding to the sensed position to the processor 105. The control unit 100 also includes an accelerometer 122 configured to sense acceleration and movement of the patient and to provide a digital signal corresponding to the sensed movement to the processor 105. In addition, an accelerometer 122 is positioned within the control unit 100. The accelerometer 122 measures the activity levels of the patient and provides the signal to the processor 105 for use in further analysis. Using an accelerometer in the implanted device indicates the activity level of the patient in conjunction with breathing and/or cardiac rate. Using the activity (accelerometer) sensor value and respiratory and/or cardiac information, the health of the respiratory system may be analyzed, evaluated and monitored. For example, if a patient's respiratory rate increases with an increase in activity and decreases with a decrease in activity, within a normal range, the patient's system will be considered functioning normally. If the patient's respiratory rate is out of range or too high while the activity sensor indicates at rest or low, then the patient may be hyperventilating. The hyperventilation breathing pattern may also be analyzed to determine if it is following a Cheyne-Stokes respirator. The control unit 100 includes a position sensor 121 configured to sense a relative position of the patient, e.g. angular position, and provide a digital signal corresponding to the sensed position to the processor 105.

Also, if the patient's respiratory rate is out of range or too high while the activity sensor indicates at rest or low, then the patient may be suffering from pulmonary edema. A determination of the severity of a patient's edema may be used to determine whether or not to treat a patient in accordance with the methods described herein.

For example, the determination may indicate that a patient should not be stimulated if it is determined to be inefficient to do so. Alternatively, information concerning pulmonary edema may indicate stimulation is desired and may also indicate specific parameters to stimulate breathing for that night. For example, if pulmonary edema is at severe level, the system may not stimulate that night. If pulmonary edema is at mid-range level, stimulate may be set to a lower amplitude and longer inspiration cycle. If pulmonary edema is at mild level, stimulation may be set to a higher amplitude and to cycles similar to intrinsic breathing.

A position sensor 121 is also located within the control unit 100 and has an output coupled to the processor 105. The position sensor senses the relative angle of the patients' position. The position sensor is used to detect a patient's relative position, e.g., horizontal, supine, or standing. An available position sensor is the Spectrol 601-1045 smart position sensor, self-contained device that provides an analog output over a full range of 360 degrees without requiring external components.

The control unit 100 further includes a ROM memory 118 coupled to the processor 105 by way of a data bus. The ROM memory 118 provides program instructions to the control unit 100 that direct the operation of the stimulator 40. The control unit 100 further comprises a first RAM memory 119 coupled via a data bus to the processor 105. The first RAM memory 119 may be programmed to provide certain stimulation parameters such as pulse or burst morphology; frequency, pulse width, pulse amplitude, duration and a threshold or trigger to determine when to stimulate. A second RAM memory 120 (event memory) is provided to store sensed data sensed, e.g., by the electrodes 21a-d 22a-d, (EMG, nerve activity or ECG), position sensor 121, movement sensors 25, 26, the accelerometer 122, blood gas sensors (e.g. pulse oximeter), blood velocity sensors, or blood pressure monitors (e.g. sensor 29 may include one or more of these sensors). These signals may be processed or analyzed and used by the control unit 100 as programmed to determine if and when to stimulate or provide other feedback to the patient or clinician. Also stored in RAM memory 120 may be the sensed waveforms for a given interval, and a count of the number of events or episodes over a given time as counted by the processor 105. The system's memory will be programmable to store: number of breathing episodes per period of time or during a time of day; pacing stimulation and length of time; the systemic auto-correction (i.e., how stimulus was adjusted, e.g., in amplitude frequency phase or waveform, to reach a desired or intrinsic level response); body resumption of breathing; the number of disorder episodes with specific durations and averages or trending information; periodic breathing events; hyperventilation episodes during supine position; number of hyperventilation episodes during sleep position; number of hyperventilation episodes during vertical position; detection of SaO2 levels, pCO2 levels, ECG information, and blood velocity or blood pressure information. These signals and information may also be compiled in the memory and downloaded telemetrically to an external device 140 when prompted by the external device 140.

A variety of signal processing techniques may be used to process the various sensed signals including those as are known to one of skill in the art. An example of the circuits of the signal processing circuit 116 corresponding to one of the EMG inputs for one of the electrodes or pairs of electrodes of the assemblies 21, 22 is illustrated schematically in FIG. 3A. An EMG signal is input into an amplifier 130 that amplifies the signal. The signal is then filtered to remove noise by filter 131. The amplified signal is rectified by a rectifier 132, is converted by an A/D converter 133 and then is integrated by integrator 134 to result in an integrated signal from which respiratory information can be ascertained. The signal output of the integrator 134 is then coupled to the processor 105 and provides a digital signal corresponding to the integrated waveform to the processor 105. The signal output of the integrator 134 is also coupled to a peak detector 135 that determines when the inspiration period of a respiratory cycle has ended and an expiration cycle has begun. The signal output of the integrator 134 is further coupled to a plurality of comparators 136, 137, 138, 139. The first comparator 136 determines when respiration (EMG signal or phrenic nerve signal) has been detected based on when an integrated signal waveform amplitude has been detected that is greater than a percentage value of the peak of an intrinsic respiratory cycle or another predetermined amount (comp 1), for example between 1-25% of the intrinsic signal. In this example, the comparator is set at a value that is 10% of the waveform of an intrinsic respiratory cycle. The second comparator 137 determines a value of the waveform amplitude (comp 2) when an integrated signal waveform amplitude has been detected that is at a predetermined percentage value of the peak of an intrinsic respiratory cycle or another predetermined amount, for example between 75%-100% of the intrinsic signal. In this example, the comparator is set at a value that is 90% of the waveform of an intrinsic respiratory cycle. From this value and the comp 1 value, the slope of the inspiration period (between 10% and 90% in this example) may be determined. This slope may provide valuable diagnostic information as it shows how quickly a patient inhales. After (or when) the peak detector detects the end of an inhalation period and the beginning of an exhalation period, the third comparator 138 determines an upper value for the waveform amplitude during active exhalation period, for example between 100% and 75% of the peak value detected by the peak detector 135. Then a lower value (comp 4) of the waveform during the exhalation period is determined by the fourth comparator 139, which compares the measured amplitude to a predetermined value, e.g. a percentage value of the peak amplitude. In this example the value is selected to be 10% of the peak value. In one embodiment this value is selected to roughly coincide with the end of a fast exhalation period. From comp 3 and comp 4 values, the slope of the exhalation period (between 10% and 90% in this example) may be determined. This slope may provide valuable diagnostic information as it shows how quickly a patient exhales. Similar processing techniques may be used with input from movement sensors 25, 26.

FIG. 3B illustrates two sequential integrated waveforms of exemplary integrated signals corresponding to two serial respiratory cycles. The waveform 170 has a baseline 170b, inspiration cycle 171, a measured inspiration cycle 172, a point of 10% of peak inspiration 173 (comp 1), a point of 90% of peak of inspiration 174 (comp 2), a peak 175 where inspiration ends and exhalation begins, and exhalation cycle 176 a fast exhalation portion 177 of the exhalation cycle 176, a 90% of peak exhalation point 178 (comp 3), a 10% of peak exhalation point 179 (comp 4), an actual respiratory cycle 180 and a measured respiratory cycle 181. The second waveform 182 is similarly shaped. The 10% inspiration 183 of the second waveform 182 marks the end of the measured respiratory cycle 181, while the 10% point 173 of the waveform 170 marks the beginning of the measured respiratory cycle 181.

The system may adjust the pace, pulse, frequency and amplitude to induce slow and elongated inspiration period; and fast and short inspiration period. The system may match the intrinsic sleep or awake time tidal volume by adjusting the output energy while sensing the EMG or nerve amplitude. This may be done gradually by frequently sensing and incrementally adjusting. The system may deliver elongated inspiration period while shortening the expiration period to control and manipulate the $SaO_2$ and $PCO_2$ levels in the blood to overcome and treat apnea. The system may deliver time and amplitude modulation output for control of inspiration and exhalation periods. To increase the inspiration period, the system may deliver fewer bursts at lower amplitudes and higher frequencies. To create a fast, short inspiration cycle, the system may deliver more of bursts at higher amplitudes. The system may deliver sequential low energy pacing output either from one or multiple electrodes to control and manage the pulmonary stretch receptor threshold levels to avoid or prevent the collapse of the upper airways. FIGS. 5A-5B illustrate a variety of exemplary stimulation bursts and resulting effective EMG/flow/tidal volume that may be used to control the various phases of the respiratory cycle including, e.g., slope of inspiration, fast exhalation, tidal volume, peak value, and rate of respiration. Other mechanisms for controlling $PCO_2$ or $SaO_2$ are described in U.S. Application entitled: "System and Method For Diaphragm Stimulation" filed on even date herewith and incorporated herein by reference.

Referring to FIGS. 5A-5B, a first intrinsic EMG waveform 550 is illustrated in FIG. 5A. A subsequent EMG waveform 551 (FIG. 6A) in response to a burst of pulses 561 (FIG. 6B) of symmetric amplitude, frequency and pulse width. A subsequent waveform 552 is illustrated (FIG. 5A) in response to burst of pulses 562 (FIG. 5B). The resulting waveform 552 (FIG. 5A) has a flatter inspiration slope and expiration slope and relatively lower peak amplitude. This particular effect may be desirable to control breathing and create a slower more gradual inspiration. The burst 562 (FIG. 5B) comprises a series of pulses increasing in amplitude and of a higher frequency that burst 561 (greater number of pulses). The subsequent EMG waveform 553 (FIG. 5A) has fewer pulses (3) and higher amplitude pulses. The effect of this burst 563 is to increase inspiration rate. The subsequent EMG waveform 554 (FIG. 5A) has a relatively slow inspiration cycle as a result of a burst 564 (FIG. 5B) with both increasing amplitudes and longer pulse widths (and greater pulse duration). These are a few examples of a multitude of possible variations of burst pulses that can be modified to control the inspiration, expiration, tidal volume (area under waveform curve) and other parameters of the respiratory cycle by modifying frequency, amplitude, pulse width of the pulses within the burst and the duration of the burst to get a desired effect. These bursts can be modified and programmed into a stimulator and may vary from patient to patient.

In FIG. 4 a circuit for an external device 140 is illustrated. The external device 140 comprises a processor 145 for controlling the operations of the external device. The processor 145 and other electrical components of the external device 140 are coordinated by an internal clock 150 and a power source 151. The processor 145 is coupled to a telemetry circuit 146 that includes a telemetry coil 147, a receiver circuit 148 for receiving and processing a telemetry signal that is converted to a digital signal and communicated to the processor 145, and a transmitter circuit 149 for processing and delivering a signal from the processor 145 to the telemetry coil 146. The telemetry coil 147 is an RF coil or alternatively may be a magnetic coil depending on what type of coil the telemetry coil 107 of the implanted control unit 100 is. The telemetry circuit 146 is configured to transmit signals to the implanted control unit 100 containing, e.g., programming or other instructions or information, programmed stimulation rates and pulse widths, electrode configurations, and other device performance details. The telemetry circuit 146 is also configured to receive telemetry signals from the control unit 100 that may contain, e.g., sensed and/or accumulated data such as sensed EMG activity, sensed nerve activity, sensed responses to stimulation, sensed position information, sensed movement information, sensed heart rate, blood pressure, blood velocity, ECG, blood gas concentration or saturation information. Other information such as frequency and time of breathing disorders, number of disorder events detected in a time interval or during a sleep cycle, parameter relating to pulmonary edema such as frequency of hyperventilation including time, patient position, and other precursor information. This information may be stored in RAM event memory 158 or may be uploaded and through an external port 153 to a computer, or processor, either directly or through a phone line or other communication device that may be coupled to the processor 145 through the external port 153. The external device 140 also includes ROM memory 157 for storing and providing operating instructions to the external device 140 and processor 145. The external device also includes RAM event memory 158 for storing uploaded event information such as sensed information and data from the control unit, and RAM program memory 159 for system operations and future upgrades. The external device also includes a buffer 154 coupled to or that can be coupled through a port to a user-operated device 155 such as a keypad input or other operation devices. Such user operation may include patient input or interaction as well as health care provider input or interaction Finally, the external device 140 includes a display device 156 (or a port where such device can be connected), e.g., for display visual, audible or tactile information, alarms or pages.

The external device 140 may take or operate in, one of several forms, e.g. for patient use, compliance or monitoring; and for health care provider use, monitoring, diagnostic or treatment modification purposes. The information may be downloaded and analyzed by a patient home unit device such as a wearable unit like a pager, wristwatch or palm sized computer. It may also alert the patient when the health care provider should be contacted, for example if there is malfunctioning of the device or worsening of the patient's condition.

The device is used to provide information to the clinicians through various communications mechanisms.

FIGS. 6A-6C and 7 illustrate exemplary precursors to breathing disorders.

FIG. 6A illustrates exemplary blood oxygen saturation levels at times 0-n through 300-n where n is a time equal to the time lag between a drop in SaO2 levels and a corresponding onset of Cheyne-Stokes hyperventilation as illustrated in FIG. 6B. As SaO2 decreases, the Cheyne stokes respiration begins and grows in amplitude and frequency. It is believed that respiration response lags the changes in SaO2. Thus, a drop in SaO2 level may be sensed, e.g., with an oximeter, as a precursor to the onset of Cheyne-Stokes respiration.

Similarly, as illustrated in FIG. 6C, as Cheyne-Stokes hyperventilation proceeds, the $PCO_2$ levels rise. It is believed that at time 120-m, the $PCO_2$ changes just before it is perceived in the medulla at which time it is believed that the Cheyne Stokes hyperventilation phase ends at time $t_1$ (FIG. 6B), where m is the time lag between the increase in PCO2 and the onset of apnea. Thus an increase in PCO2 may be sensed, as a precursor to the onset of apnea, e.g., with a PCO2 sensor placed adjacent an airway.

FIG. 7 is a schematic of what is known as a Cheyne-Stokes breathing pattern. From time $t_0$ to $t_1$ a characteristic hyperventilation pattern precedes a period of apnea from time $t_1$ to $t_2$. After a period of time ($t_1$ to $t_2$), the hyperventilation pattern resumes from time $t_2$ to $t_3$, and again, a period of apnea begins. This pattern may repeat itself a number of times. The Cheyne-Stokes characteristic hyperventilation pattern is one where the amplitude and frequency of breaths increases and then decreases. From $t_0$ to $t_1$ and from $t_2$ to $t_3$, this pattern is illustrated and forms an envelope 200. The patterns of breathing from $t_0$ to $t_1$ and from $t_2$ to $t_3$, are precursors to episodes of apnea (e.g., $t_1$ to $t_2$).

The Cheyne-Stokes pattern illustrated in FIG. 7 may be sensed using the signal processor and waveform analysis described with respect to FIGS. 3A-3B. The analysis may also be done in a number of ways using a variety of other signal processing techniques. For example, the envelope or a portion of the envelope may be detected and compared to a characteristic envelope. If the envelope correlates to a sufficient degree to a characteristic envelope as programmed into the processor, then a Cheyne-Stokes pattern is identified. Such signal comparison and correlation techniques as are known to one of skill in the art may be used to sense and determine when a Cheyne-Stokes hyperventilation pattern is most probably present.

According to one embodiment of the invention, a series of inspiration waveforms are analyzed as described with reference to FIGS. 3A-3B to determine if a breathing pattern is a precursor to a breathing disorder, in this particular example, to identify if Cheyne-Stokes hyperventilation as a precursor to apnea is occurring.

The pattern of the amplitude changes may be used to verify a Cheyne-Stokes respiration pattern. Additionally or alternatively, frequency changes may be used to verify a Cheyne-Stokes respiration pattern.

The peak value 175 of the inspiration cycle indicates the depth of the breath. The measured peak value is stored for a plurality of cycles. The trend of the peak value may be calculated by a processor. If the trend is increasing then begins decreasing, a Cheyne-Stokes like pattern may be identified.

The calculated slope of the inspiration cycle, the slope of the exhalation cycle, the measured respiratory cycle, and/or the measured exhalation period correlate to the frequency of breathing. A plurality of one or more of these parameters may be stored for a plurality of cycles. If the frequency and/or amplitude of breathing increases and decreases according to a preset range of values, a Cheyne-Stokes pattern may be identified.

The controller 100 detects a precursor event sensed by electrodes on assemblies 21, 22. Similarly, the controller 100 detects a precursor event to Cheyne-Stokes sensed by $SaO_2$ or $PCO_2$ sensors (sensor 29). The controller responds to the detection according to a program in RAM 120.

In one variation, the response is to stimulate the diaphragm to capture or control the breathing rate by stimulating the diaphragm. The stimulation may be initiated during the sensed precursor. For example, the stimulation may be initiated during the Cheyne-Stokes hyperventilation portion. Thus the Cheyne-Stokes hyperventilation breathing is arrested, a specific breathing pattern in induced, and apnea is prevented. Alternatively, the diaphragm stimulator may be initiated at the end of Cheyne-Stokes at the onset of apnea to control breathing. The stimulation may also be initiated at another time prior to the expected onset of the breathing disorder.

FIG. 8 illustrates an example of a sensing of Cheyne-Stokes hyperventilation as a precursor to apnea and treatment to prevent apnea by stimulating breathing. At time ta0, diaphragm breathing is observed at a baseline normal level. At time $ta_1$ Cheyne-Stokes respiration is initiated. At time $ta_2$ the Cheyne-Stokes respiration has reached a peak value that is at least as high as threshold amplitude A1. The threshold amplitude A1 is the amplitude threshold at or above which an episode of apnea will very likely occur. This threshold amplitude A1 may be set at an absolute value or at a percentage of the baseline value. The value may be determined on a patient by patient basis after observing one or more Cheyne-Stokes respirations with and/or without subsequent apneas. At time $ta_3$, the end portion of the Cheyne-Stokes respiration is sensed, for example when the peak value for the respiration is at or below threshold amplitude A1. The end portion of Cheyne-Stokes may be determined, for example, by sensing a drop in amplitude to the threshold amplitude A1, by sensing a drop in frequency, by identifying a point on the respiration envelope using previous recorded Cheyne-Stokes patterns or using a model, or by sensing a drop in $PCO_2$ just prior to the onset of apnea. At time $ta_3$, the stimulator according to the invention stimulates to control the diaphragm and breathing until time $ta_4$ when the resumption of normal breathing is confirmed.

FIG. 9 illustrates an example of treatment of Cheyne-Stokes hyperventilation by stimulating breathing shortly before, during or after the onset of Cheyne-Stokes hyperventilation. At time $tb_0$, diaphragm breathing is observed at a baseline normal level. At time $tb_1$ just before the onset of Cheyne-Stokes hyperventilation, the $SaO_2$ levels may have been sensed as falling indicating Cheyne-Stokes respiration will be initiated. Stimulation may occur at this time in response to sensing the drop in SaO2 as a precursor to Cheyne-Stokes. If not stimulated prior to such time, then at time $tb_2$ Cheyne Stokes hyperventilation begins. At time $tb_3$ Cheynes-Stokes respiration has been sensed, for example by detecting an increase in amplitude and or frequency or respiration to a preset threshold A3, by identifying a point on the respiration envelope using previous recorded Cheyne-Stokes patterns or using a model. At time $tb_3$, the stimulator according to the invention stimulates to control the diaphragm and breathing until time $tb_4$ when the resumption of normal breathing is confirmed.

FIG. 10A or 10B are examples of periodic breathing patterns that may precede Cheyne-Stokes and/or apnea events. The pattern may be an EMG signal that has been processed. This periodic breathing may occur, for example, during periods of wakefulness and/or during the day prior to an evening where there is a likelihood of Cheyne-Stokes and/or apnea. Or, this breathing pattern may occur just prior to a Cheyne-Stokes and/or apnea event or events. One or more precursor events such as the periodic breathing over a period of time, is sensed and stored in RAM 119, the processor determines a likelihood of a breathing disorder occurring according to a program stored in RAM 120. The RAM program may do one of a number of things. The sensitivity or detection threshold for detecting a breathing disorder, may be increased, for example by lowering a threshold. Also after determining periodic breathing, the system may be armed to look for a particular pattern such as the initiation of Cheyne-Stokes hyperventilation (FIG. 9) or the slowing of the Cheyne-Stokes hyperventilation (FIG. 8). Alternatively, the RAM program may automatically turn on breathing control (for stimulation continuously or at intervals) for a given period of time and/or at a particular time of day, e.g. when sleep is occurring.

FIG. 11 illustrates an example of a sensing of Cheyne-Stokes hyperventilation as a precursor to apnea and treatment of apnea by stimulating breathing. At time $tc_0$, diaphragm breathing is observed at a baseline normal level. At time $tc_1$ Cheyne-Stokes respiration is initiated. At time $tc_2$, the end of the Cheyne-Stokes respiration is sensed, for example: by sensing a drop in amplitude and or frequency to a preset threshold; by identifying a point on the respiration envelope using previous recorded Cheyne-Stokes patterns or using a model; or by sensing the end of Cheyne-Stokes hyperventilation. At time $tc_2$, the stimulator according to the invention stimulates to control the diaphragm and breathing until time $tc_3$ when the resumption of normal breathing is confirmed.

FIG. 12 illustrates the operation of a precursor sensor and breathing treatment device according to one variation. The diaphragm EMG is sensed during the day 400. Characteristic precursor breathing is observed 401, such as, for example, the periodic breathing illustrated in FIG. 10. The system is armed 402 and set to control breathing during the nighttime. Breathing is controlled at nighttime 403, for example, by continuously or intermittently stimulating breathing to elicit a desired breathing morphology. Night time may be identified by detecting when sleeping is occurring or by a real time clock.

FIG. 13 illustrates the operation of another variation of a precursor sensor and breathing treatment device. A pre-disorder EMG is sensed and stored 500, e.g. in RAM 120. A breathing disorder is detected 501, e.g. Cheyne-Stokes respiration or apnea. The pre-disorder EMG is flagged and saved 502. The steps 500-502 may be repeated a number of times, for example a plurality of nighttimes in sequence or until a breathing disorder has been detected at a plurality of times, e.g. different nighttimes. A model of the pre-disorder EMG is then created 503, for example, using statistical or probabilistic modeling. Probabilistic sensing is set using the model 504 to sense a subsequent characteristic precursor pre-disorder EMG. The EMG is then monitored 505. A pre-disorder characteristic precursor EMG is sensed 506. The stimulator then controls breathing to prevent the disorder 507.

Stimulation of breathing may be set to control blood gases and thereby treat breathing disorders. The $PCO_2$ may be controlled by controlling the minute ventilation (Minute ventilation is the product of respiratory rate and tidal volume). For example, $PCO_2$ is increased if minute ventilation is decreased.

Safety mechanisms may be incorporated into any stimulation device in accordance with the invention. The safety feature disables the device under certain conditions. Such safety features may include a patient or provider operated switch, e.g. a magnetic switch. In addition a safety mechanism may be included that determines when patient intervention is being provided. For example, the device will turn off if there is diaphragm movement sensed without an EMG as the case would be where a ventilator is being used.

While the invention has been described with reference to particular embodiments, it will be understood to one skilled in the art that variations and modifications may be made in form and detail without departing from the spirit and scope of the invention.

What is claimed is:

1. A device for treating a sleep breathing disorder comprising:
   at least one electrode configured to sense a parameter corresponding to a precursor to onset of a sleep breathing disorder where intrinsic breathing is present, and the at least one electrode, or an additional electrode, configured to deliver an electrical signal targeting diaphragm or phrenic nerve tissue to cause contraction of at least a portion of a diaphragm to control breathing in response to a sensed precursor, to prevent or mitigate a sleep breathing disorder in a subject;
   a control unit comprising:
   a stimulation pulse generator configured to deliver electrical stimulation to the tissue through the at least one electrode to thereby elicit a diaphragm response to control a breathing of the subject;
   wherein the control unit is programmed to detect the precursor and to deliver the stimulation in response to information sensed by the at least one electrode by controlling electrical stimulation delivered to the tissue through the electrode, wherein the control unit is further programmed to control the stimulation pulse generator to deliver a burst or series of pulses as the electrical stimulation; and wherein upon detecting a precursor to onset of a sleep breathing disorder, the control unit is further programmed to provide at least one electrical stimulation, monitor the breathing of the subject for a first interval of time and provide at least one electrical stimulation if the breathing is not as desired, monitor the breathing for at least a subsequent second interval of time longer than the first interval, sense for normalized breathing, compare the breathing to intrinsic breathing, and to further provide at least one electrical stimulation if the breathing is not as desired or cease the at least one electrical stimulation if breathing is as desired.

2. The device of claim 1 wherein the control unit is programmed to cause the at least one electrode and/or an additional electrode to electrically stimulate to cause diaphragm contraction prior to onset of the breathing disorder.

3. The device of claim 1 wherein the control unit is programmed to cause the at least one electrode and/or an additional electrode to electrically stimulate to control at least one respiration parameter to manipulate minute ventilation.

4. The device of claim 1 wherein the control unit is programmed to cause the at least one electrode and/or an additional electrode to electrically stimulate to manipulate inspiration duration with respect to intrinsic inspiration duration.

5. The device of claim 1 wherein the control unit is programmed to cause the at least one electrode and/or an additional electrode to electrically stimulate to elicit a longer inspiration cycle with respect to an intrinsic respiration cycle.

6. The device of claim 1 wherein the control unit is programmed to cause the at least one electrode and/or an additional electrode to electrically stimulate to control the peak of inspiration of a respiration waveform.

7. The device of claim 6 wherein the control unit is programmed to cause the at least one electrode and/or an additional electrode to electrically stimulate to elicit a slower rate of inspiration with a lower peak of inspiration.

8. The device of claim 1 wherein the control unit is programmed to cause the at least one electrode and/or an additional electrode to electrically stimulate to control slope of an inspiration curve.

9. The device of claim 1 wherein the control unit is programmed to cause the at least one electrode and/or an additional electrode to electrically stimulate to control the rate of inspiration.

10. The device of claim 1 wherein the control unit is programmed to cause the at least one electrode and/or an additional electrode to electrically stimulate to control the rate of exhalation.

11. The device of claim 1 wherein the control unit is programmed to cause the at least one electrode and/or an additional electrode to electrically stimulate to control exhalation duration.

12. The device of claim 1 wherein the control unit is programmed to cause the at least one electrode and/or an additional electrode to electrically stimulate to inhibit respiratory drive take over control of breathing for a period of time and to provide a therapeutic stimulation according to a therapeutic stimulation protocol during the period of time.

13. The device of claim 1 wherein the control unit is programmed to cause the at least one electrode and/or an additional electrode to electrically stimulate to manipulate a respiration waveform to control the partial pressure of carbon dioxide of the patient's blood.

14. The device of claim 1 wherein the control unit is programmed to cause the at least one electrode and/or an additional electrode to electrically stimulate to manipulate a respiration waveform to control the level of oxygen in the patient's blood.

15. The device of claim 1 wherein the control unit is programmed to cause the at least one electrode and/or an additional electrode to electrically stimulate during at least one exhalation period of a breathing cycle and to inhibit central respiratory drive.

16. The device of claim 15 wherein the control unit comprises a stimulation protocol programmed into the control unit configured to provide a series of sequential stimulations subsequent to providing stimulation during the exhalation period.

17. The device of claim 1 wherein the precursor to onset of a sleep breathing disorder is selected from the group consisting of periodic breathing, hyperventilation, Cheyne-Stokes, and an abnormal breath immediately preceding Cheyne-Stokes.

18. A system for treating a subject comprising:
at least one electrode configured to sense at least one parameter corresponding to the at least one precursor to the onset of a sleep breathing disorder during a period;
a control unit comprising:
  a) an analyzer coupled to the at least one electrode configured to sense respiration, wherein the analyzer is programmed to recognize a respiratory pattern where intrinsic breathing is present corresponding to a likelihood of a sleep breathing disorder occurring at a time after the period; and
  b) an electrical stimulator programmed to deliver electrical stimulation to at least one of said electrodes directly targeting a subject's diaphragm or phrenic nerve to cause contraction of at least a portion of a diaphragm to control breathing prior to onset or to mitigate a breathing disorder in response to the analyzer recognizing the respiratory pattern corresponding to a likelihood of a breathing disorder occurring a time after the period,
wherein the electrical stimulator is further programmed to deliver a burst or series of pulses as the electrical stimulation; and
wherein upon sensing of a precursor to the onset of a sleep breathing disorder, the control unit is further programmed to provide at least one electrical stimulation, monitor the breathing of the subject for a first interval of time and provide at least one electrical stimulation if the breathing is not as desired, monitor the breathing for at least a subsequent second longer interval of time, sense for normalized breathing, and to further provide at least one electrical stimulation if the breathing is not as desired or cease the at least one electrical stimulation if the breathing is as desired.

19. A method for treating a sleep breathing disorder in a subject having intrinsic breathing, comprising the steps of:
sensing a precursor to a breathing disorder in the subject where intrinsic breathing is present;
evaluating the sensed precursor via an analyzer which is programmed to recognize a respiratory pattern corresponding to a sleep breathing disorder; and,
if the analyzer recognizes the respiratory pattern corresponding to the sleep breathing disorder, delivering an electrical stimulation signal comprising a burst or series of pulses through an electrode to diaphragm or phrenic nerve tissue to contract at least a portion of a diaphragm in response to the sensed precursor thereby preventing an onset or mitigating the sleep breathing disorder;

monitoring the breathing of the subject for a first interval of time and providing at least one electrical stimulation if the breathing is not as desired, monitoring the breathing for at least a subsequent second interval of time longer than the first interval, sensing for normalized breathing, and providing at least one electrical stimulation signal if the breathing is not as desired or ceasing the at least one electrical stimulation if the breathing is as desired.

20. The method of claim 19 further comprising providing the stimulation prior to onset of a breathing disorder.

21. The method of claim 19 further comprising providing the stimulation to cause diaphragm contraction prior to onset of the breathing disorder.

22. The method of claim 19 further comprising providing the stimulation to control at least one respiration parameter to manipulate minute ventilation.

23. The method of claim 19 further comprising providing the stimulation to manipulate inspiration duration with respect to intrinsic inspiration duration.

24. The method of claim 19 further comprising providing the stimulation to elicit a longer inspiration cycle with respect to an intrinsic respiration cycle.

25. The method of claim 19 further comprising providing the stimulation to control the peak of inspiration of a respiration waveform.

26. The method of claim 19 further comprising providing the stimulation to elicit a slower rate of inspiration with a lower peak of inspiration.

27. The method of claim 19 further comprising providing the stimulation to control slope of an inspiration curve.

28. The method of claim 19 further comprising providing the stimulation to control the rate of inspiration.

29. The method of claim 19 further comprising providing the stimulation to control the rate of exhalation.

30. The method of claim 19 further comprising providing the stimulation to control exhalation duration.

31. The method of claim 19 further comprising providing the stimulation to inhibit respiratory drive to take over control of breathing for a period of time and providing a therapeutic stimulation according to a therapeutic stimulation protocol during the period of time.

32. The method of claim 19 further comprising providing the stimulation is provided to manipulate a respiration waveform to control the partial pressure of carbon dioxide of the patient's blood.

33. The method of claim 19 further comprising providing the stimulation to manipulate a respiration waveform to control the level of oxygen in the patient's blood.

34. The method of claim 19 further comprising providing the stimulation to stimulate during at least one exhalation period of a breathing cycle and to inhibit central respiratory drive.

35. The method of claim 34 wherein the stimulation comprises a stimulation protocol providing a series of sequential stimulations subsequent to providing stimulation during the exhalation period.

36. A device for treating a breathing disorder comprising:
at least one electrode configured to sense a parameter corresponding to a precursor to onset of a breathing disorder in a subject having intrinsic breathing, and to deliver an electrical signal directly targeting diaphragm or phrenic nerve tissue to cause contraction of at least a portion of a diaphragm to control breathing in response to a sensed precursor, to prevent or mitigate a breathing disorder in the subject; and, a control unit programmed to deliver electrical stimulation to the tissue through the at least one electrode to thereby elicit a diaphragm response to control a breathing of the subject;

an analyzer being programmed to detect the precursor and to respond to information sensed by the at least one electrode by delivering a burst or series of pulses as the electrical stimulation to the tissue through the electrode; and wherein upon sensing of a precursor to onset of a sleep breathing disorder, the device is further programmed to provide at least one electrical stimulation, monitor the breathing of the subject for a first interval of time and provide at least one electrical stimulation if the breathing is not as desired, monitor the breathing for at least a subsequent second interval of time longer than the first interval, sense for normalized breathing, and to further provide at least one electrical stimulation if the breathing is not as desired or cease the at least one electrical stimulation if the breathing is as desired.

37. The device of claim 36 wherein the control unit is configured to electrically stimulate to cause diaphragm contraction prior to onset of the breathing disorder.

38. The device of claim 36 wherein the control unit is configured to electrically stimulate to control at least one respiration parameter to manipulate minute ventilation.

39. The device of claim 36 wherein the control unit is configured to electrically stimulate to manipulate inspiration duration with respect to intrinsic inspiration duration.

40. The device of claim 36 wherein the control unit is configured to electrically stimulate to elicit a longer inspiration cycle with respect to an intrinsic respiration cycle.

41. The device of claim 36 wherein the control unit is configured to electrically stimulate to control the peak of inspiration of a respiration waveform.

42. The device of claim 41 wherein the control unit is configured to electrically stimulate to elicit a slower rate of inspiration with a lower peak of inspiration.

43. The device of claim 36 wherein the control unit is configured to electrically stimulate to control slope of an inspiration curve.

44. The device of claim 36 wherein the control unit is configured to electrically stimulate to control the rate of inspiration.

45. The device of claim 36 wherein the control unit is configured to electrically stimulate to control the rate of exhalation.

46. The device of claim 36 wherein the control unit is configured to electrically stimulate to control exhalation duration.

47. The device of claim 36 wherein the control unit is configured to electrically stimulate to inhibit respiratory drive take over control of breathing for a period of time and to provide a therapeutic stimulation according to a therapeutic stimulation protocol during the period of time.

48. The device of claim 36 wherein the control unit is configured to electrically stimulate to manipulate a respiration waveform to control the partial pressure of carbon dioxide of the patient's blood.

49. The device of claim 36 wherein the control unit is configured to electrically stimulate to manipulate a respiration waveform to control the level of oxygen in the patient's blood.

50. The device of claim 36 wherein the control unit is configured to electrically stimulate to stimulate during at least one exhalation period of a breathing cycle and to inhibit central respiratory drive.

51. The device of claim 50 wherein the control unit comprises a stimulation protocol programmed into the device configured to provide a series of sequential stimulations subsequent to providing stimulation during the exhalation period.

* * * * *